United States Patent
Fauss et al.

(10) Patent No.: US 12,154,077 B2
(45) Date of Patent: Nov. 26, 2024

(54) USER INTERFACE FOR DISPLAYING PATIENT HISTORICAL DATA

(71) Applicant: MEDICAL INFORMATICS CORPORATION, Houston, TX (US)

(72) Inventors: Emma K. Fauss, Houston, TX (US); Alexander Csicsery-Ronay, Taos, NM (US); Vincent Gagne, Houston, TX (US)

(73) Assignee: Medical informatics Corp., Houston, TX (US)

( * ) Notice: Subject to any disclaimer, the term of this patent is extended or adjusted under 35 U.S.C. 154(b) by 971 days.

(21) Appl. No.: 15/621,324

(22) Filed: Jun. 13, 2017

(65) Prior Publication Data
US 2017/0357764 A1   Dec. 14, 2017

Related U.S. Application Data

(60) Provisional application No. 62/349,571, filed on Jun. 13, 2016.

(51) Int. Cl.
*G16H 10/60* (2018.01)
*A61B 5/00* (2006.01)
(Continued)

(52) U.S. Cl.
CPC .......... *G06Q 10/109* (2013.01); *A61B 5/339* (2021.01); *A61B 5/7435* (2013.01); *G16H 40/63* (2018.01); *G16H 10/60* (2018.01); *G16H 40/67* (2018.01)

(58) Field of Classification Search
None
See application file for complete search history.

(56) References Cited

U.S. PATENT DOCUMENTS

| 8,941,657 B2 | 1/2015 | Agarwal et al. |
| 9,538,933 B2 | 1/2017 | Helfenbein et al. |

(Continued)

FOREIGN PATENT DOCUMENTS

| JP | 2003319913 A | 11/2003 |
| JP | 2004194996 A | 7/2004 |

(Continued)

OTHER PUBLICATIONS

Michaela Spitzer et al., BoxPlotR: a web tool for generation of box plots, Feb. 2014, Nature Methods, vol. 11, pp. 121-122 (Year: 2014).*

(Continued)

*Primary Examiner* — Shahid Merchant
*Assistant Examiner* — Andrew E Lee
(74) *Attorney, Agent, or Firm* — Schafer IP Law; Richard A. Schafer

(57) ABSTRACT

A graphical user interface of a medical patient monitoring system allows clinical personnel to view and manipulate historical patient data in ways not available in traditional patient monitoring systems. The graphical user interface allows zooming in or out on the historical patient data, with a format of the data adjusted at certain zoom levels. A plurality of lanes of displayed historical patient data may be displayed in the graphical user interface, and a plurality of signals may be displayed in a single lane. An electrocardiogram strip view may be enabled to present historical patient data in the form of a traditional strip view if desired.

35 Claims, 19 Drawing Sheets
(16 of 19 Drawing Sheet(s) Filed in Color)

(51) Int. Cl.
  *A61B 5/339* (2021.01)
  *G06Q 10/109* (2023.01)
  *G16H 40/63* (2018.01)
  *G16H 40/67* (2018.01)

(56) References Cited

U.S. PATENT DOCUMENTS

| | | | |
|---|---|---|---|
| 2002/0077863 A1 | 6/2002 | Rutledge et al. | |
| 2007/0271067 A1* | 11/2007 | Cohn | G01R 31/31708 |
| | | | 702/183 |
| 2009/0005703 A1 | 1/2009 | Fasciano | |
| 2009/0054743 A1 | 2/2009 | Stewart | |
| 2011/0169644 A1* | 7/2011 | Muhsin | G08B 25/008 |
| | | | 340/573.1 |
| 2012/0075103 A1 | 3/2012 | Powell et al. | |
| 2012/0278099 A1 | 11/2012 | Kelly et al. | |
| 2013/0024130 A1* | 1/2013 | Zahniser | G16H 40/63 |
| | | | 702/21 |
| 2013/0045685 A1 | 2/2013 | Kiani | |
| 2013/0096649 A1* | 4/2013 | Martin | G06F 19/3418 |
| | | | 607/60 |
| 2013/0152005 A1 | 6/2013 | McLaren et al. | |
| 2013/0271470 A1* | 10/2013 | Moore | G16H 10/60 |
| | | | 345/440.1 |
| 2014/0132413 A1* | 5/2014 | Fox | A61B 5/0022 |
| | | | 340/573.1 |
| 2015/0243040 A1* | 8/2015 | Ben-Oni | G06T 11/206 |
| | | | 345/629 |
| 2016/0063182 A1 | 3/2016 | Srivastava et al. | |
| 2016/0321904 A1* | 11/2016 | Johnson | G06F 19/3418 |
| 2017/0042488 A1* | 2/2017 | Muhsin | A61B 5/742 |
| 2018/0033169 A1* | 2/2018 | de Waele | G16H 40/63 |
| | | | 702/21 |
| 2018/0286500 A1* | 10/2018 | Sole Guerra | G16H 10/60 |

FOREIGN PATENT DOCUMENTS

| | | |
|---|---|---|
| JP | 2011078640 A | 4/2011 |
| JP | 2012520144 A | 9/2012 |
| JP | 2014506162 A | 3/2014 |
| JP | 2015000174 A | 1/2015 |
| WO | 2012158720 A1 | 11/2012 |

OTHER PUBLICATIONS

The International Search Report and The Written Opinion of the International Searching Authority; mail date Sep. 21, 2017, 13 pages.

Winston Chang, R Graphics Cookbook, Nov. 28, 2013, p. 139, O'Reilly Japan, Inc., Japan.

* cited by examiner

USER INTERFACE FOR DISPLAYING PATIENT HISTORICAL DATA

TECHNICAL FIELD

The present invention relates to the field of medical data processing, and in particular to a user interface for displaying patient historical data.

BACKGROUND ART

Physicians, nurses, and other clinical practitioners often have a desire to review historical patient data for patients. Conventional medical informatics systems have had limited capability at best for viewing historical patient data, in part because capture and storage of historical patient data has been difficult, but also because user interfaces for allow viewing of historical patient data were unable to show data with desired flexibility and in desired combinations. Clinical practitioners would find a better user interface for displaying historical patient data desirable.

BRIEF DESCRIPTION OF DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
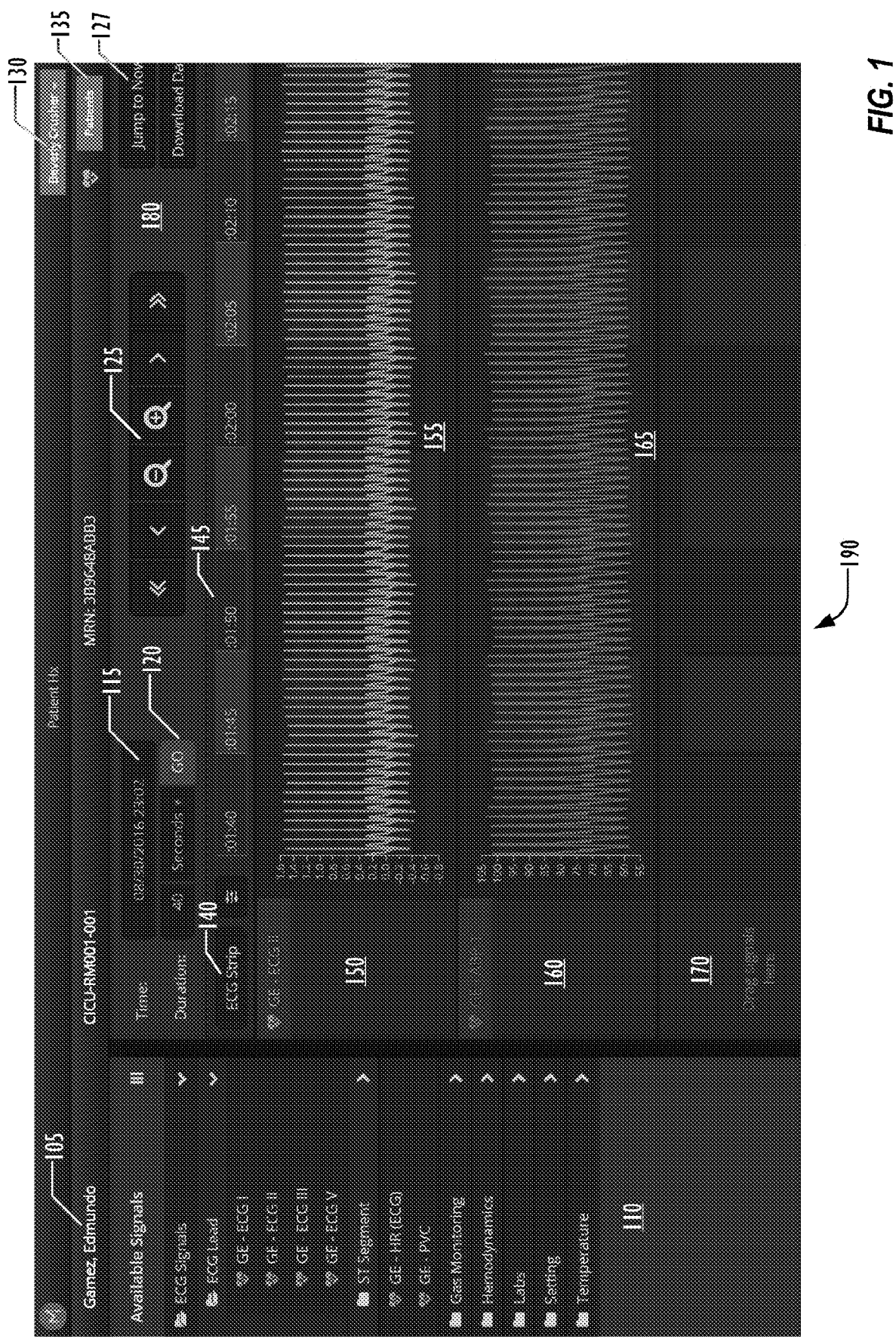
FIG. 1 is a screenshot illustrating a user interface with a plurality of lanes of historical patient data according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

The terms "a," "an," and "the" are not intended to refer to a singular entity unless explicitly so defined, but include the general class of which a specific example may be used for illustration. The use of the terms "a" or "an" may therefore mean any number that is at least one, including "one," "one or more," "at least one," and "one or more than one."

The term "or" means any of the alternatives and any combination of the alternatives, including all of the alternatives, unless the alternatives are explicitly indicated as mutually exclusive.

The phrase "at least one of" when combined with a list of items, means a single item from the list or any combination of items in the list. The phrase does not require all of the listed items unless explicitly so defined.

As used herein, the term "a computer system" can refer to a single computer or a plurality of computers working together to perform the function described as being performed on or by a computer system.

As used herein, the term "processing element" can refer to a single hardware processing element or a plurality of hardware processing elements that together may be programmed to perform the indicated actions. The hardware processing elements may be implemented as virtual hardware processing elements of a virtual programmable device hosted on a physical hardware device. Instructions that when executed program the processing element to perform an action may program any or all of the processing elements to perform the indicated action. Where the processing element is one or more multi-core processors, instructions that when executed program the processing element to perform an action may program any or all of the multiple cores to perform the indicated action.

As used herein, the term "medium" can refer to a single physical medium or a plurality of media that together store the information described as being stored on the medium.

As used herein, the term "memory" can refer to a single memory device or a plurality of memory devices that together store the information described as being stored on the medium. The memory may be any type of storage device, including random access memory, read-only memory, optical and electromechanical disk drives, etc.

As used herein, the term "graphical user interface" ("GUI") refers to an interactive graphical display that provides the ability for human-machine interaction, allowing users to control the operation of the machine through the use of graphical widgets that allow for interactions appropriate to the kind of data they represent.

As used herein, the term "widget" refers to a software control element of interaction with a GUI, such as a button or a scroll bar. In addition to the displayed software control element, the widget includes software to perform the activity indicated by interaction with the widget, such as by clicking a mouse button or pressing a key on a keyboard.

As used herein, the term "lane" refers to a horizontal or vertical region of a GUI that is used for displaying one or more types of data. Embodiments of the GUI may allow for a plurality of lanes, and in some embodiments, the GUI may allow the user to vary the number of lanes of data that are displayed by the GUI.

As used herein, the term "pane" refers to a section of a GUI, typically a section containing graphical widgets having a common or related functionality. Panes may contain one or more lanes in some embodiments.

As used herein, the term "web-based" refers to software in which a client GUI runs in a web browser. In various embodiments, some processing may be performed by a web server that provides web pages to a client executing the web browser software, but other processing may be performed by the client using client-side software contained or linked to by the web page.

As used herein, the term "historical patient data" refers to patient data that has been collected corresponding to a patient in a medical facility over a period of time, including physiological data that may be collected in real time at the current time. The display of the historical patient data may or may not include real-time current patient data depending on the time period displayed in the GUI. Patient data may include any signals captured and managed by the underlying platform, such as device data, alarms, alarm limits, physiological data, laboratory results, medications, and Admission, Discharge and Transfer (ADT) records.

As used herein, an "actor" is a doctor, nurse, or other clinical personnel assigned to a clinical unit and responsible for the care of the patient. The actor is sometimes referred to as a "user" and the terms should be considered interchangeable.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

Systems described below provide a medical patient monitoring system that provides a way for clinical personnel to view historical patient physiological data in a convenient, flexible web-based graphical user interface that can automatically adjust the interface to better display the data at different time scales, while allowing the practitioner control over the data to be displayed. In addition, certain kinds of data may be presented in a "strip view" similar to how traditional paper strips of physiological data have been displayed, but with additional capabilities.

In some embodiments, trends of vital data recorded, alarms, laboratory results, and medications may be displayed. In other embodiments, non-scaled electrocardiogram (ECG) and other event data may be presented for review, with the capability of being exported into an electronic medical records system, providing another important patient history review capability.

The user interface described herein allows for displaying historical patient data, including but not limited to device data, alarms, alarm limits, physiologic data, laboratory results, medications, and Admission, Discharge and Transfer (ADT) records—any signals captured and managed by the underlying platform. In one embodiment, the underlying platform is a Sickbay Platform provided by Medical Informatics Corp. of Houston, Texas. The actor can view previous patient admissions or the current admission. Once a patient is selected, in one embodiment, the user is presented with a view of the default patient data signals for the past 12 hours.

In some embodiments, the underlying platform may calculate for historical patient data automatically for various periods such as every hour and every day. These statistics may then be viewable in the GUI 100. Available statistics in various embodiments may include: (a) Mean; (b) Standard Deviation (SD); (c) Maximum Value; (d) 3rd Quartile; (e) Median; (f) 1st Quartile; and (g) Minimum Value. Other statistical measures may be provided as desired.

The actor may zoom out to a year's worth of data or zoom down into a view of 1 second of data (a single heart beat). These limits are illustrative and by way of example only, and other limits on the zooming ability may be provided. The actor can determine which data to review and is provided with analytics/summary data where appropriate.

FIG. 1 is a screenshot illustrating a graphical user interface 100 for displaying historical patient data according to one embodiment. The GUI 100 in one embodiment is a web-based GUI, displayed in web page in a web browser. For purposes of clarity, browser elements outside of the web page that comprises the GUI are omitted from FIG. 1, but one of skill in the art will understand that the omitted elements may include browser elements known to the art. The GUI 100 may be implemented in a machine- and operating system-independent way, allowing the same GUI to function on different types of client devices.

As illustrated in FIG. 1, the GUI 100 includes a patient pane 105 that displays patient-specific information such as the patient's name or other patient identifying information, and location information such as a bed identifier. In some embodiments, if a patient has moved beds, an indication of that bed change or location change may be visible in the patient pane 105. In some embodiments, additional data such as admission data for the patient may be displayed in the patient pane 105. In some embodiments, a patient selection widget 135 may provide the ability for a user, such as a physician or nurse, to select which patient's data to display in the GUI 100. In some embodiments, such as in embodiments where a display is used by multiple clinical staff, pre-configurations of the GUI may be provided by use of a widget 130, allowing selection of what user is currently using the GUI, and an initial configuration of the GUI based on prior stored configuration information or upon a default configuration. In some embodiments, the patient selected for display may be a former patient or an earlier admission of a current patient.

In one embodiment, a configuration pane 180 provides widgets that control the display of the historical patient data.

As illustrated in FIG. 1, configuration pane 180 comprises a time widget 115 that displays a data and time corresponding to the historical patient data visible in the GUI 100. This may be one or more of a start time, end time, or another time such as a midpoint of the time period. A duration widget 120 allows the user to define the length of time to be displayed in the GUI, such as a number of seconds, minutes, hours, days, months, etc. A zoom and pan widget 125 may allow the actor to change a zoom level or to scroll the display to earlier or later times. Some embodiments may also allow the actor to use direct interaction techniques such as dragging a patient data to pan through the patient data, or zooming the patient data view. Implementations may include a widget 127 to allow a "jump to now" function, quickly scrolling the patient data to real time.

In one embodiment, an ECG strip widget 140 may allow an actor to switch a view of the patient data to a strip view, as described in more detail below.

A timeline 145 may display information about the time corresponding to the current time period being displayed, with markings on the timeline that are automatically selected based on the duration. In some embodiments, a period of time prior to the time indicated in time widget 115 and a period of time after the time indicated in time widget 115 are displayed. The period of time prior and period of time after may be different amounts. For example, as illustrated in FIG. 1, a 40 second time period around Aug. 30, 2016 at 23:02 is displayed, displaying 20 seconds prior to 23:02 and 20 second starting at 23:02. If a duration of a different time scale, such as hours, is selected in the duration widget, the timeline is automatically adjusted to one appropriate for the duration.

A navigation pane 110 in one embodiment allows displaying of available historical patient data that can be selected for view in the GUI 100. Illustrated in an expanded state in FIG. 1, navigation pane may display available historical patient data in any convenient way, such as in the folder-like structure illustrated in FIG. 1, including subfolders of available patient data.

In one embodiment, only available historical patient data at the current zoom level is presented to the actor in the navigation pane 110. In other embodiments, unavailable historical patient data may be listed in the navigation pane 110, but may be indicated as unavailable. E.g., if waveform signals cannot be selected at durations greater than 5 minutes, some embodiments may represent the signal by a dimmed signal name.

Preferably, embodiments may distinguish between signals that are not available at that zoom level and those signals that are not available for this patient. E.g., just because arterial blood pressure (APB) is a signal the system records, if APB was not recorded for this patient during their stay, it should not be displayed in the list of signals.

A signals pane 190 provides an area for one or more lanes of historical patient data display along the timeline 145. As illustrated in FIG. 1, two lanes, 150 and 160, have been selected to show an ECG lead signal (trace 155) and an arterial blood pressure signal (trace 165) for the patient. For historical patient data that is not waveform signal-based, other types of displays of the data may be used as described below. In FIG. 1, a third lane 170 indicates that additional patient data may be selected in the navigation pane 110 and dragged to lane 170, resulting in display of the selected patient data in lane 170. If a folder or subfolder is dragged from the navigation pane 110 to a lane, all of the patient data types may be superimposed on each other in the lane. In one embodiment, the lane is automatically scaled so that all the historical patient data is visible in the lane. In other embodiments, the actor may control the scaling to provide a desired view of the patient data, even if the scaling results in some portion of the data becoming invisible in the pane.

The arrangement and widgets of the embodiment illustrated in FIG. 1 are illustrative and by way of example only, and other arrangements and widgets may be used as desired. For example, FIG. 2 illustrated another embodiment of a GUI 200 in which a tabbed view is used for navigation pane 230 that extends across the bottom of the GUI 200 instead of the folder view of navigation pane 110 in FIG. 1.

Figure 2:
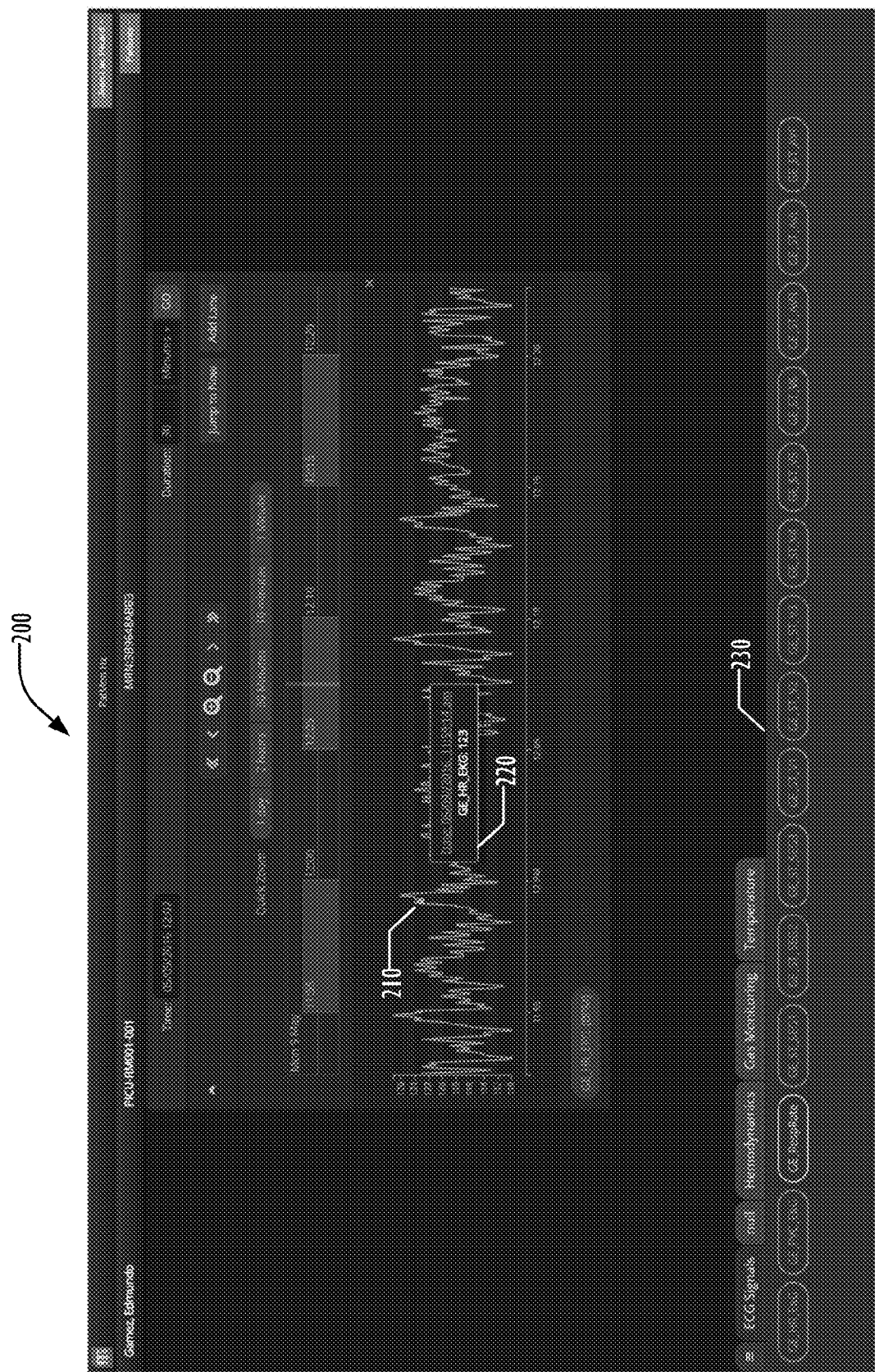
FIG. 2 is a screenshot illustrating a user interface with only a single lane of historical patient data according to a different embodiment.

By selecting a portion of the historical patient data shown in the GUI 100 or 200, such as by clicking or hovering a mouse at point 210 on the ECG signal illustrated in FIG. 2, in some embodiments a pop-up display 220 may be made visible, providing detail information about the patient data at the indicated point.

In some embodiments, the actor may be provided a way to tag or mark events or segments of data, including annotating the tagged or marked events or segments. In some embodiments, the tagged or marked events or segments of data may provide a way to jump from one tag to the next or previous tagged event or segment. Some embodiments may allow sharing or sending tag information to other actors for review.

Figure 3:
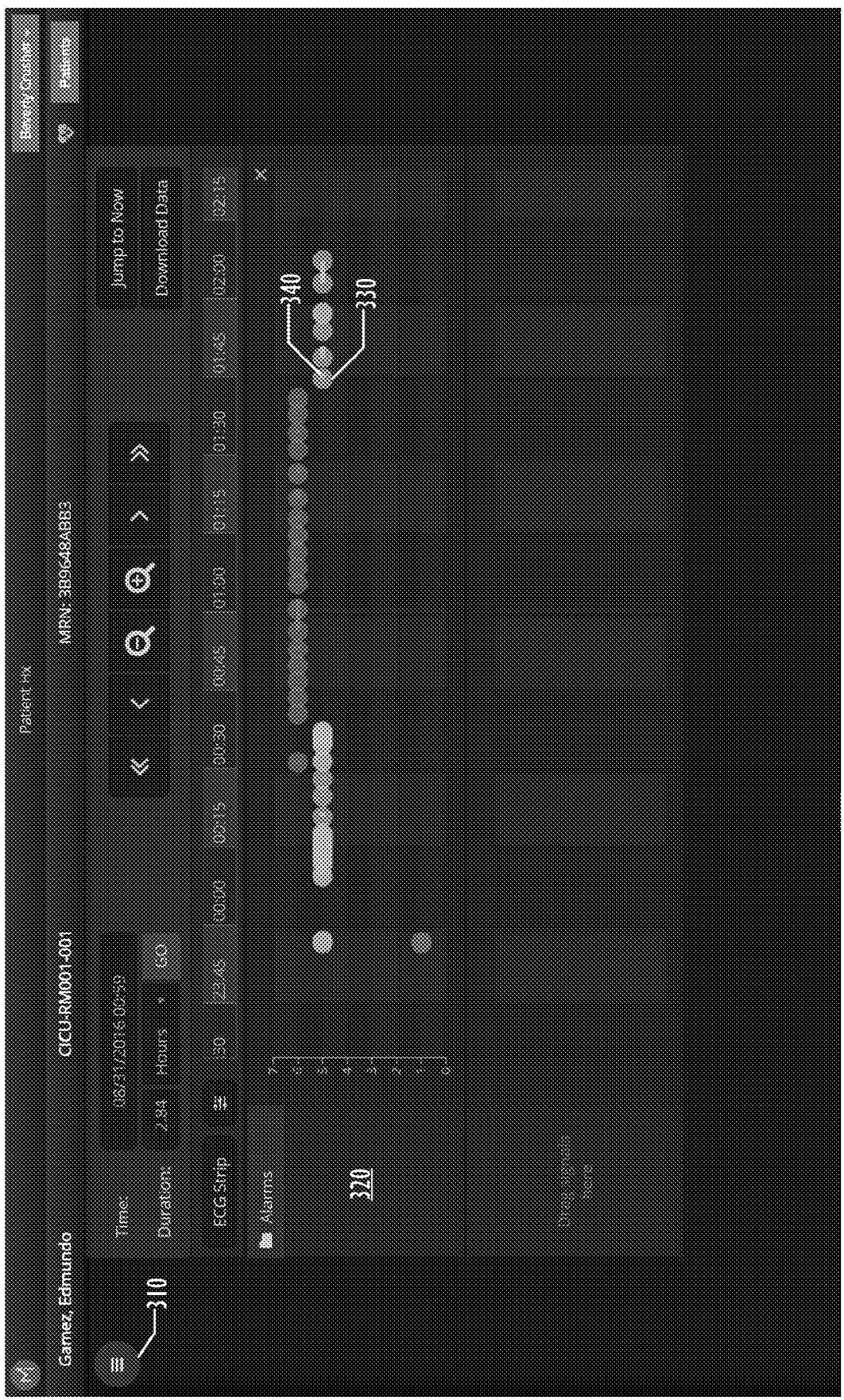
FIG. 3 is a screenshot illustrating the user interface of FIG. 1 illustrating historical alarm data according to one embodiment.

FIG. 3 is a screenshot of the embodiment of FIG. 1 illustrating a lane 320 on which alarm data for the patient has been displayed. Instead of a waveform as in the signals in lanes 150 and 160 of FIG. 1, each alarm is indicated in this example as a dot or small circle, such as dot 330. The shape of the alarm indications is illustrative and by way of example only, and other shapes for each alarm indication can be used. In this example, the color of the alarms corresponds to the alarm level, so for example a gray dot is illustrated at alarm level 1, while yellow dots are shown for alarm level 5 and red dots for alarm level 6. This corresponds to a common clinical facility color coding of alarm information.

In addition to the dot or circle indicating the alarm, a small bar 340 is included in one embodiment to indicate the length of time the patient remained in alarm status with that alarm. The small bar 340 begins at the center of the dot, illustrating the when the alarm occurred, and extends to the right for the length of time the alarm status persisted. As with the waveform type signals illustrated in FIG. 1, the dots 330 are placed on the timeline, although displayed a point graph, rather than a continuous waveform.

In FIG. 3, the navigation pane 110 has been closed, typically by clicking on the indicator 310. Interacting with the indicator 310 again would open the navigation pane 110 again.

Figure 4:
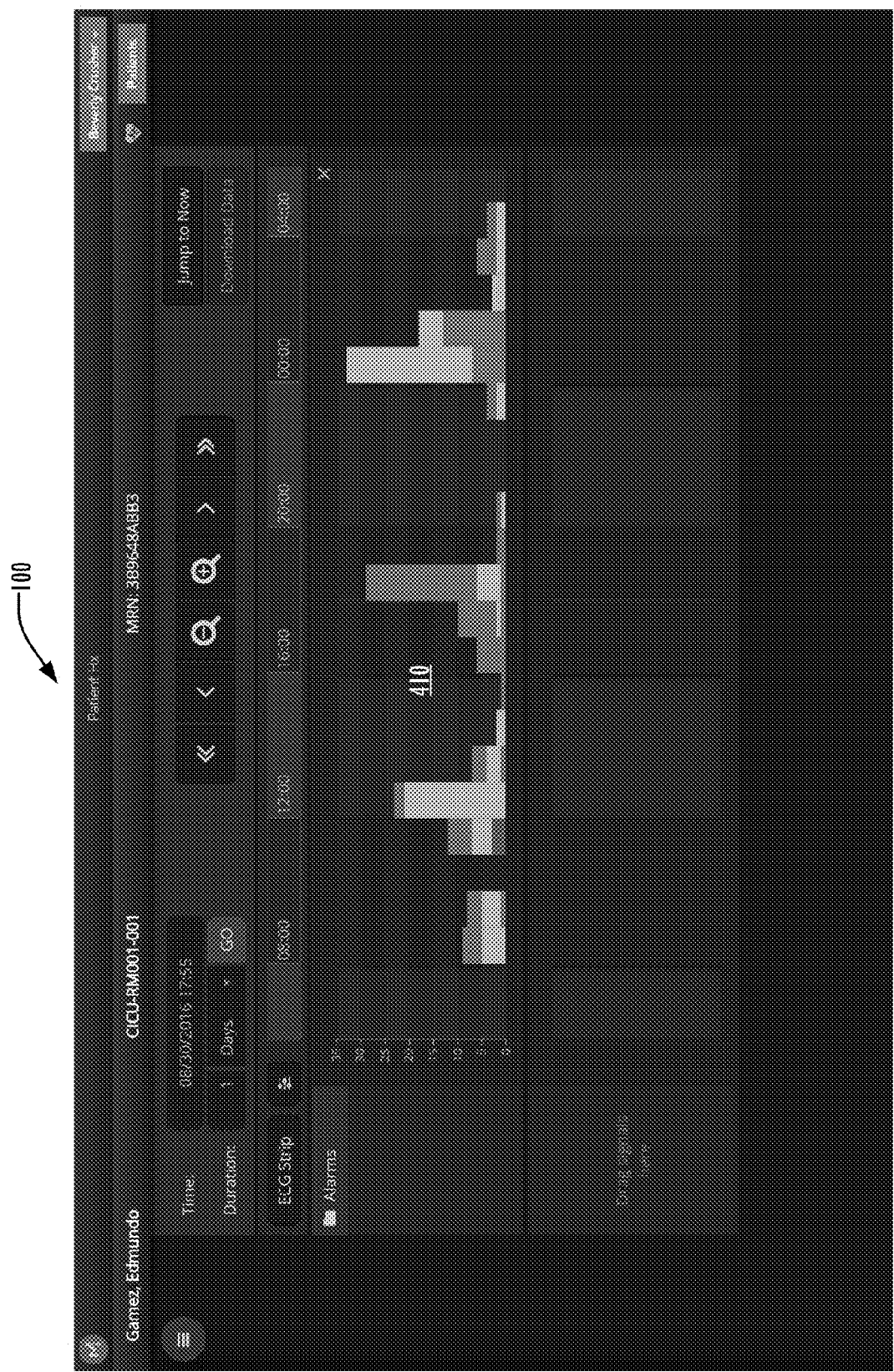
FIG. 4 is a screenshot illustrating the user interface of FIG. 1 displaying a lane of histograms of historical alarm data according to one embodiment.

FIG. 4 is a screenshot illustrating the GUI 100 with a collection of alarms illustrated in a lane as a histogram 410. This illustrates that an actor may drag a folder from the navigation pane 110 (now closed) to a lane, bringing all of the historical patient data for that folder into the lane. In FIG. 4, instead of displaying individual alarm occurrences, a histogram 410 provides a display of how many alarm occurred during each time slot on the timeline, in this example a 4 hour period, with the duration set to 1 day.

Figure 5:
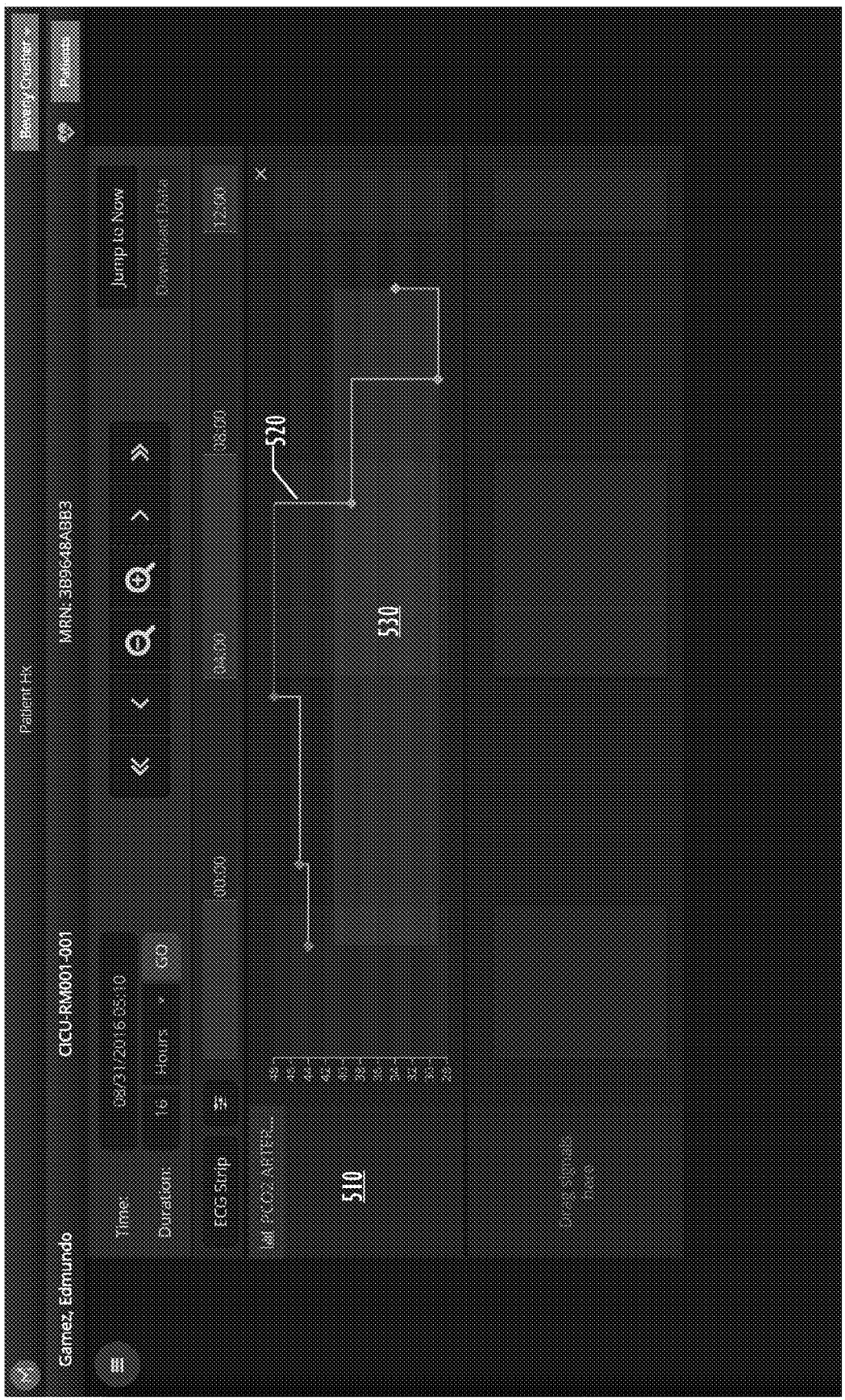
FIG. 5 is a screenshot illustrating the user interface of FIG. 1 with a lane displaying historical lab or med data according to one embodiment.

Another type of data is illustrated in the screenshot of FIG. 5. In this example, 16 hours of lab test results are illustrated in lane 510 as graph line 520. Each lab test result is indicated as a dot on the graph line 520, with straight lines connecting each dot to its predecessor and successor lab result indicator. An area 530 indicates the range of normal results for this particular lab test, letting the actor easily see that the lab results in this example were out of the normal range during a portion of the displayed timeline (before 00:00 and through a point somewhere between 04:00 and 08:00), at which point they dropped into the normal range, even though varied from time to time thereafter.

Although in the example of FIG. 5, the historical patient data illustrated on line 520 is lab result data, the same technique can be used to record the provisioning of medications to the patient in one embodiment.

Figure 6:
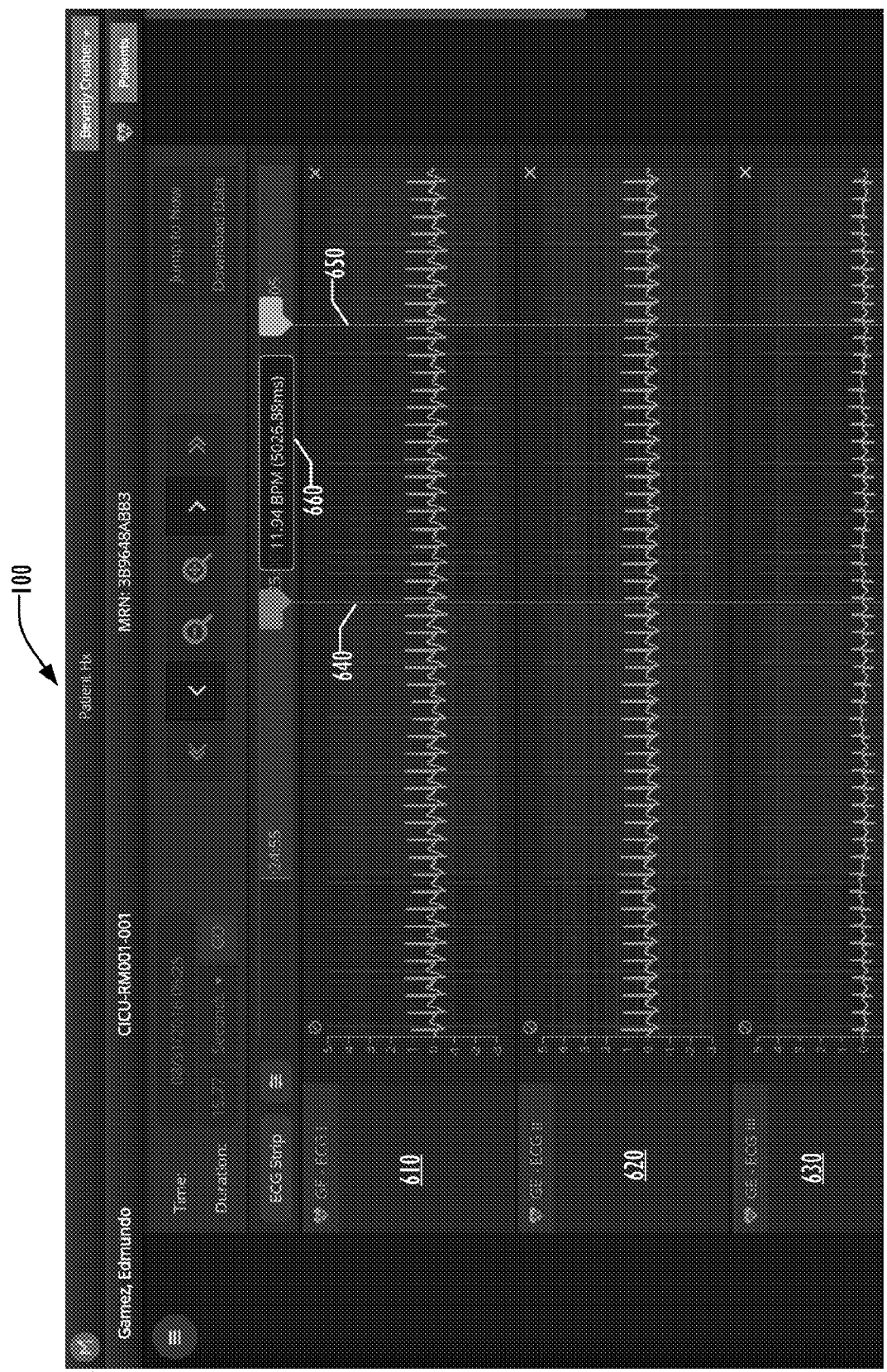
FIG. 6 is a screenshot illustrating the user interface of FIG. 1 with three lanes in a strip view according to one embodiment.

Turning now to FIG. 6, three lanes 610-630 are displayed, each with ECG traces displayed in a strip view, with an underlying grid for ease of measurement. In this configuration, caliper lines 640 and 650 may be inserted over the lanes 610-630, allowing the actor to see information such as is displayed in pop-up area 660. In this example, the GUI 100 displays that the patient's heart rate was 11.94 beats per minute during the 5026.88 ms time period circumscribed by the caliper lines 640 and 650. By scrolling or panning the historical patient data signals in lanes 610-630 underneath the caliper lines 640 and 650, the actor can, for example, easily determine that the patient's heart rate increased or decreased relative to the time period where the caliper lines 640 and 650 were originally placed, and the magnitude of that change. This provides a much easier technique than the traditional technique of measuring using a ruler on a strip view.

In strip view the GUI 100 adjusts the time scale to the correct ECG ratio as displayed on a traditional patient monitor, locking this aspect ratio for proper ECG analysis. The actor can only move forward and backward in time or adjust the time window, however the aspect ratio remains constant.

In some embodiments, the strip view information of FIG. 6 can be printed in a conventional strip view format on paper. A method to annotate and export strips to an electronic medical records system as a .pdf or .jpeg file with a uniform resource locator (URL) hyperlinking back to the historical view app may be provided in some embodiments. In some embodiments, medical notes are not stored by the platform, but are only included in the exported strip. This can enabled with a button or other user interaction element.

Figure 7:
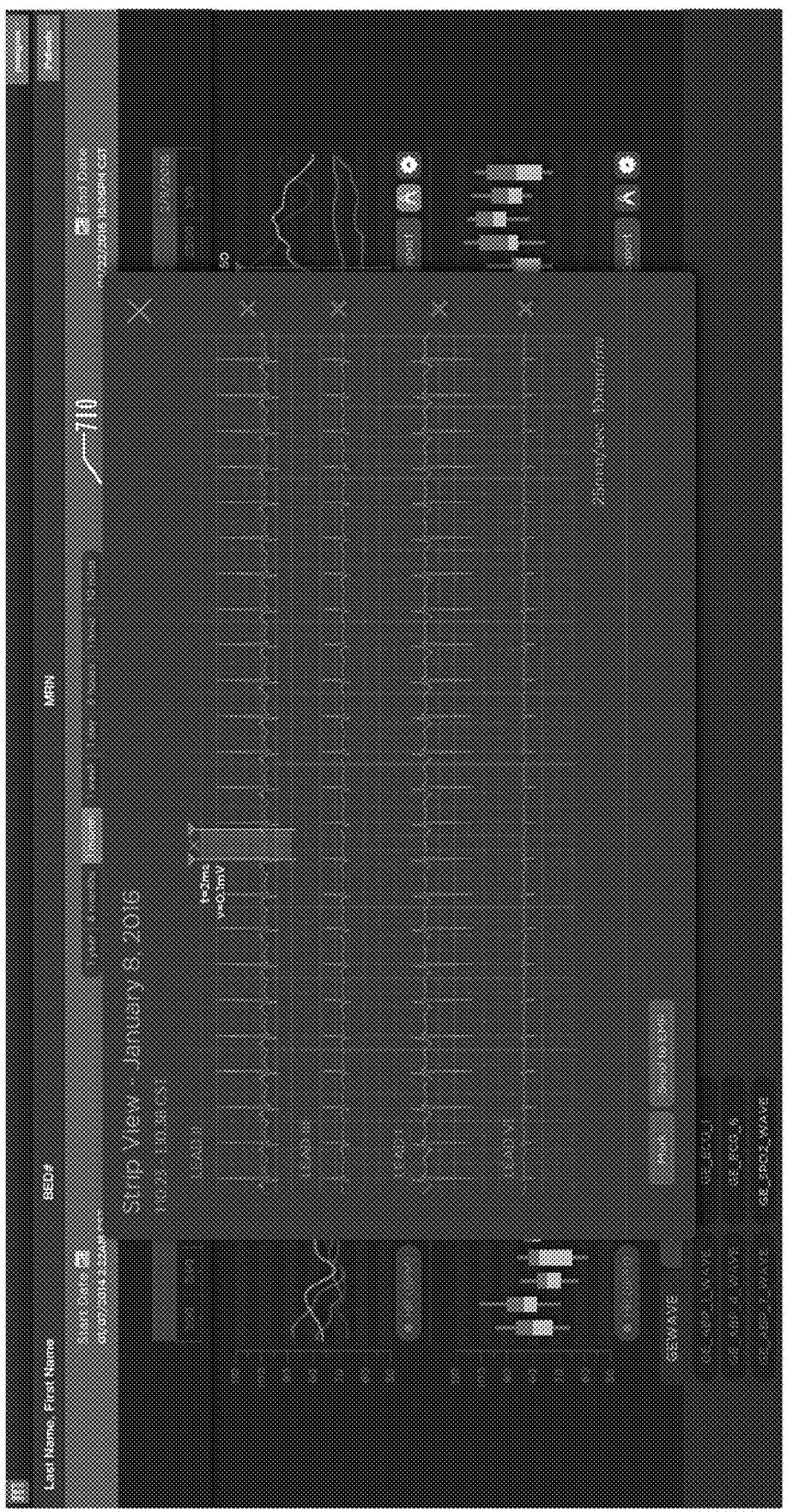
FIG. 7 is a screenshot illustrating a strip view according to another embodiment.

Although the strip view lanes of FIG. 6 are displayed in main window of the GUI 100, other embodiments may use modal windows, such as the modal window 710 illustrated in FIG. 7. FIG. 7 also illustrates alternate graphical widgets corresponding to the caliper lines 640 and 650 of FIG. 6, in this alternate embodiment extending across only one of the waveforms, instead of all of the waveforms as in FIG. 6.

Figure 8:
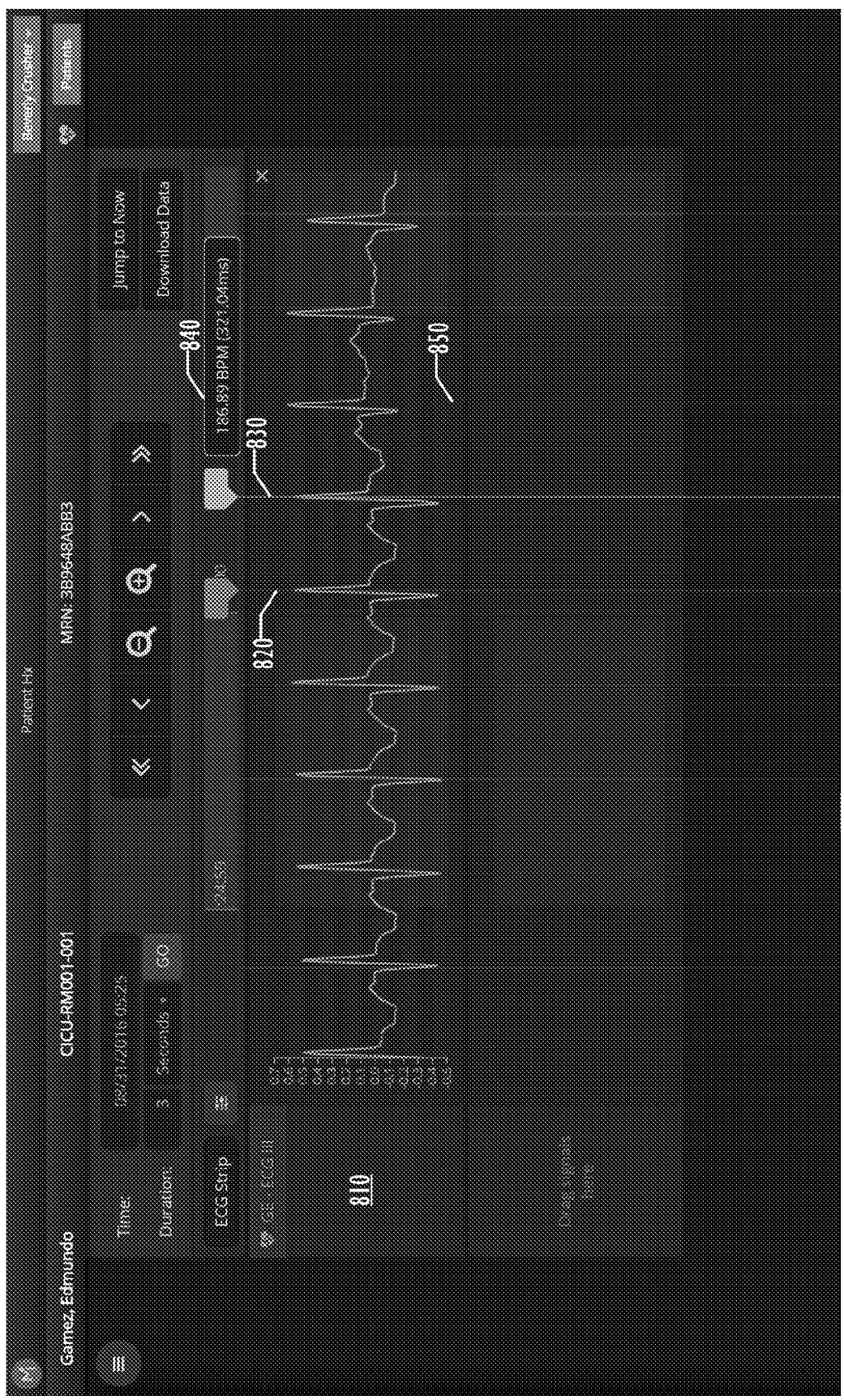
FIG. 8 is a screenshot illustrating the user interface of FIG. 1 with a lane of historical electrocardiogram data according to one embodiment.

The caliper lines technique of FIGS. 6 and 7 in some embodiments may be used in a non-strip view configuration, such as is illustrated in the screenshot of FIG. 8. In this example, a timeline based on a 3 second duration employs caliper lines 820 and 830, indicating a heartrate of 186.89 beats per minute (BPM) during the 321.04 ms time period (displayed in area 840) indicated by caliper lines 820 and 830. In addition, shadow caliper lines 850 may be placed at equal time spans across the timeline, giving a visual indication of changes in the periodicity of the waveform illustrated in lane 810, even without the underlying grid of a strip view display. Thus, even without measuring, the actor can easily see that the heartrate of this patient changed during this three second duration.

Figure 9:
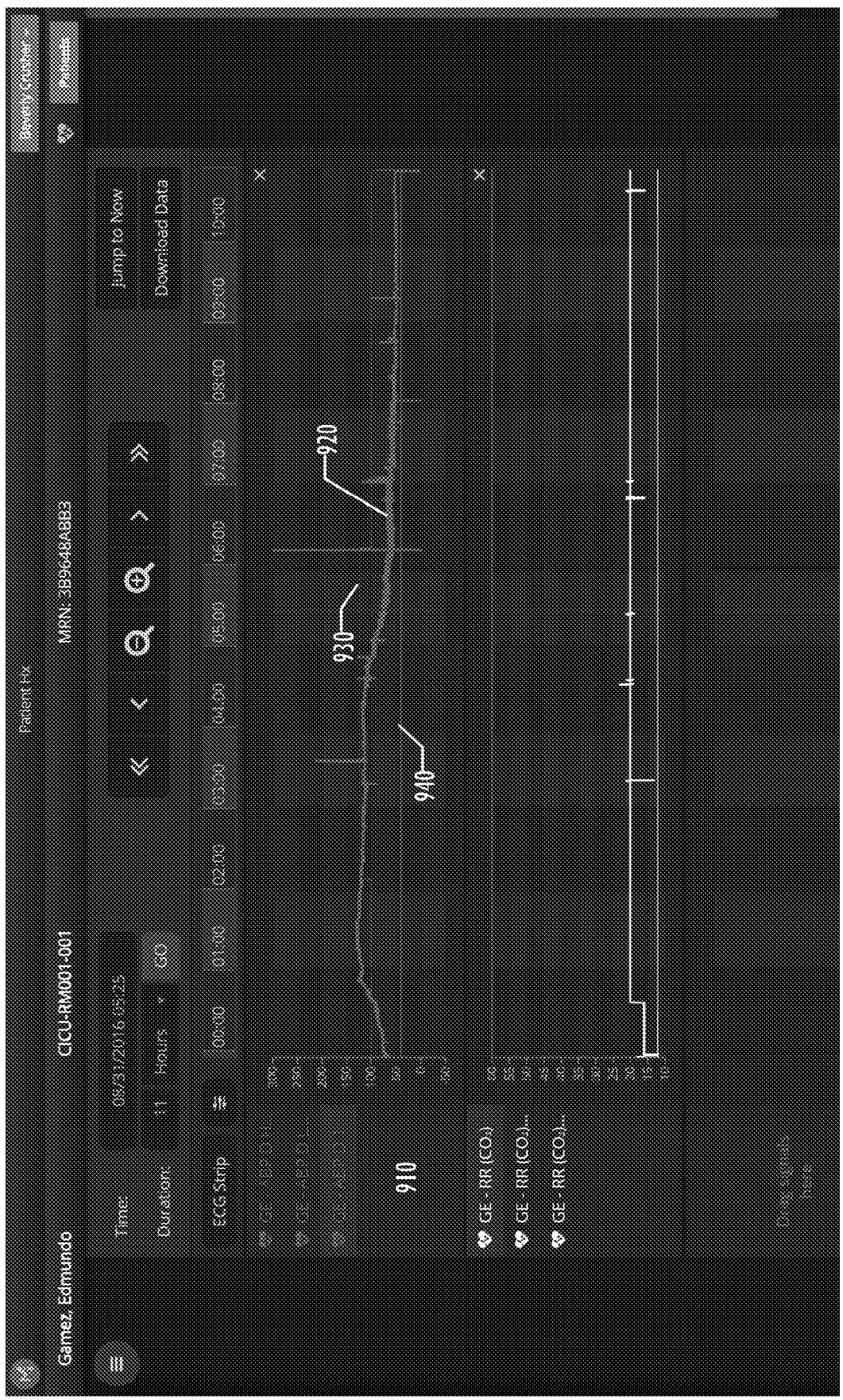
FIG. 9 is a screenshot illustrating the user interface of FIG. 1 with a lane of historical patient data and guardrails according to one embodiment.

Turning now to FIG. 9, alarm thresholds may be displayed as guardrails or threshold values appropriate to the historical patient data. In this example lane 910 illustrates an arterial blood pressure waveform 920, guardrails 930 and 940 illustrate the alarm settings throughout the duration displayed in lane 910. Where alarm settings are updated, the guardrails reflect those updated alarm settings at the corresponding times, thus in this example, the lower guardrail 940 remains constant throughout the duration on the timeline, while the upper guardrail 930, corresponding to an upper alarm setting, was raised shortly after 02:00, then decreased shortly after 06:00. These guardrails provide the actor with an easy way to view when the displayed historical patient data was in alarm status during the time period of concern.

Figure 10:
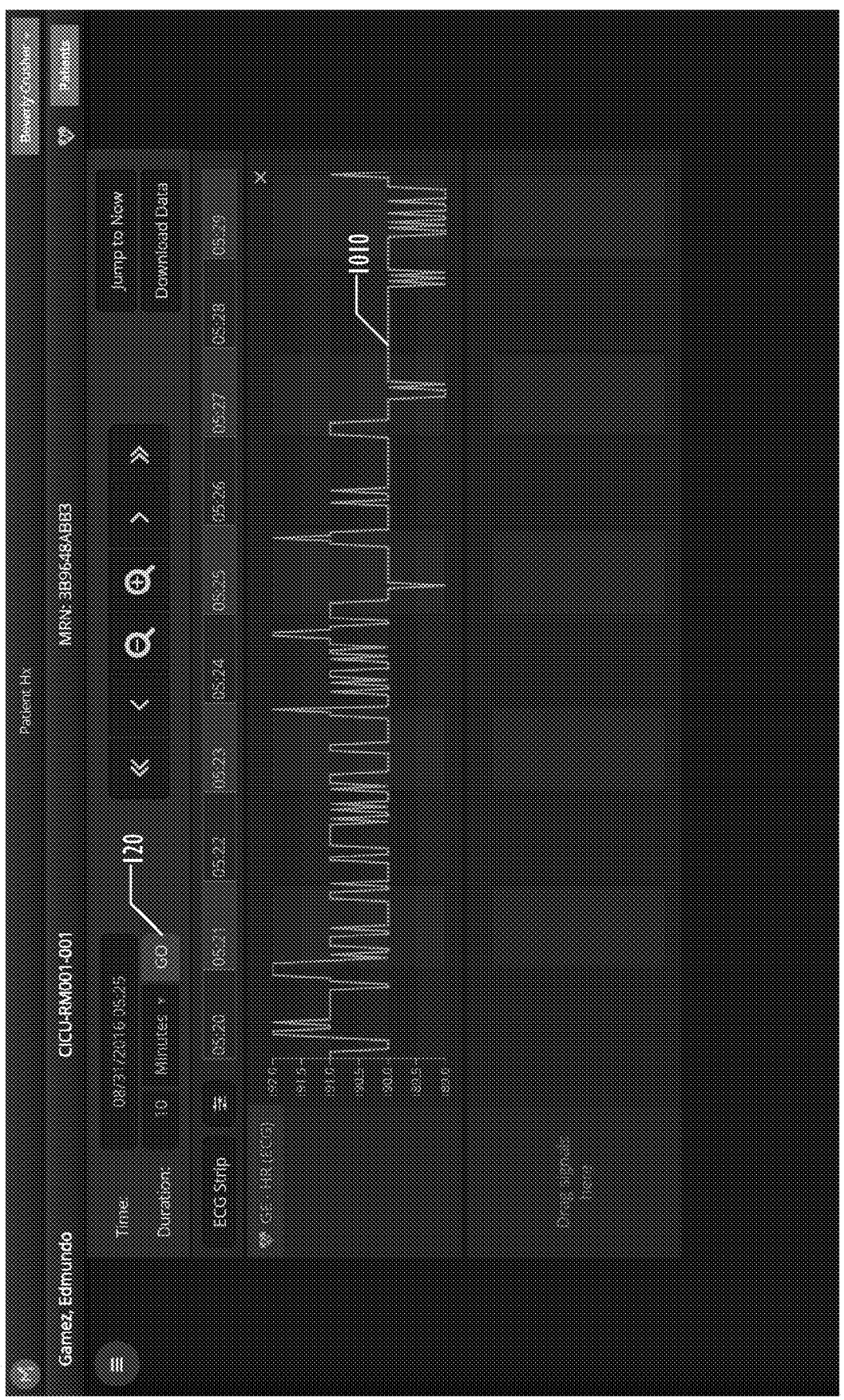
FIGS. 10-15 are screenshots illustrating the user interface of FIG. 1 with a lane of historical patient data at a plurality of time durations according to one embodiment.
Figure 11:
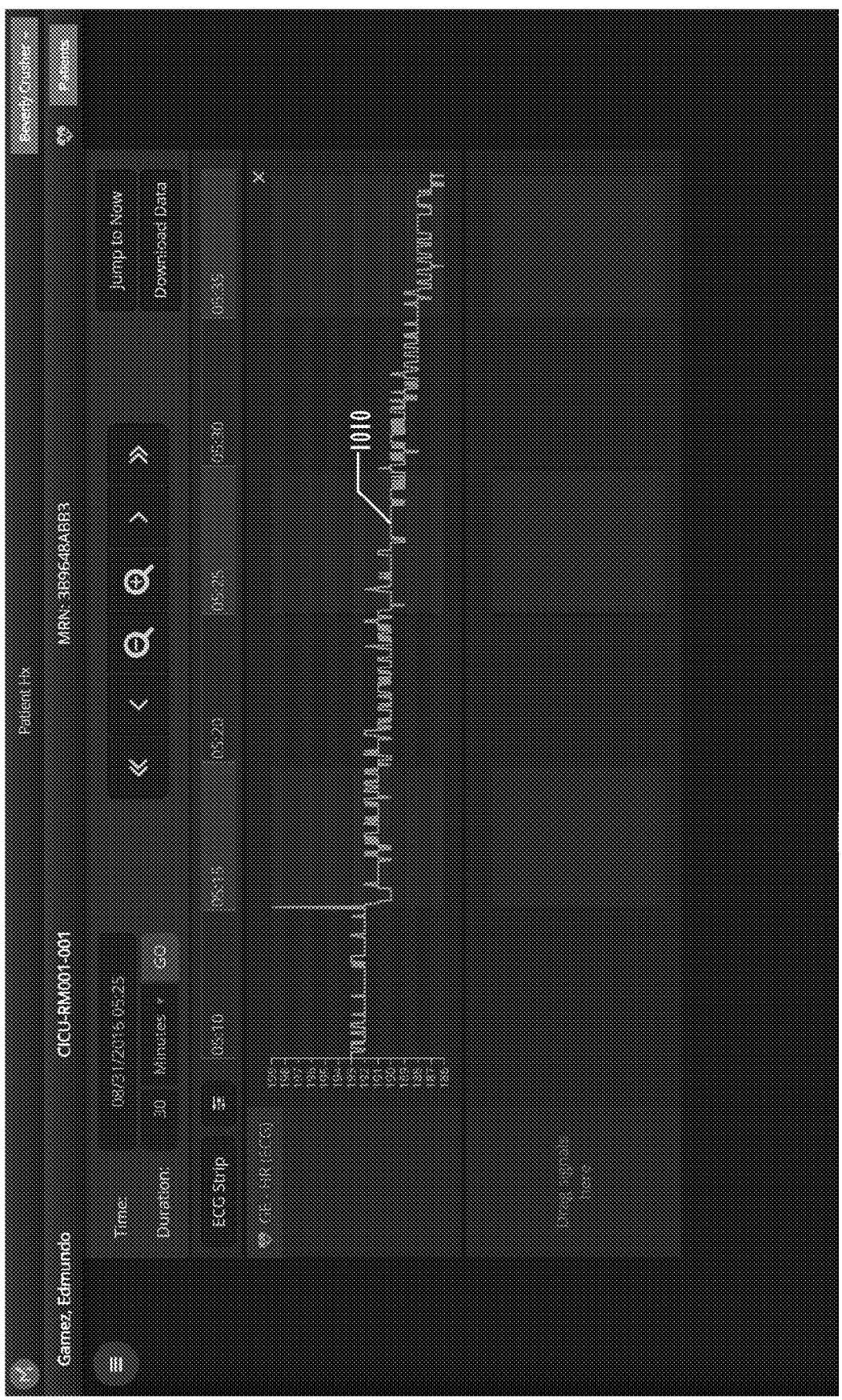
Figure 12:
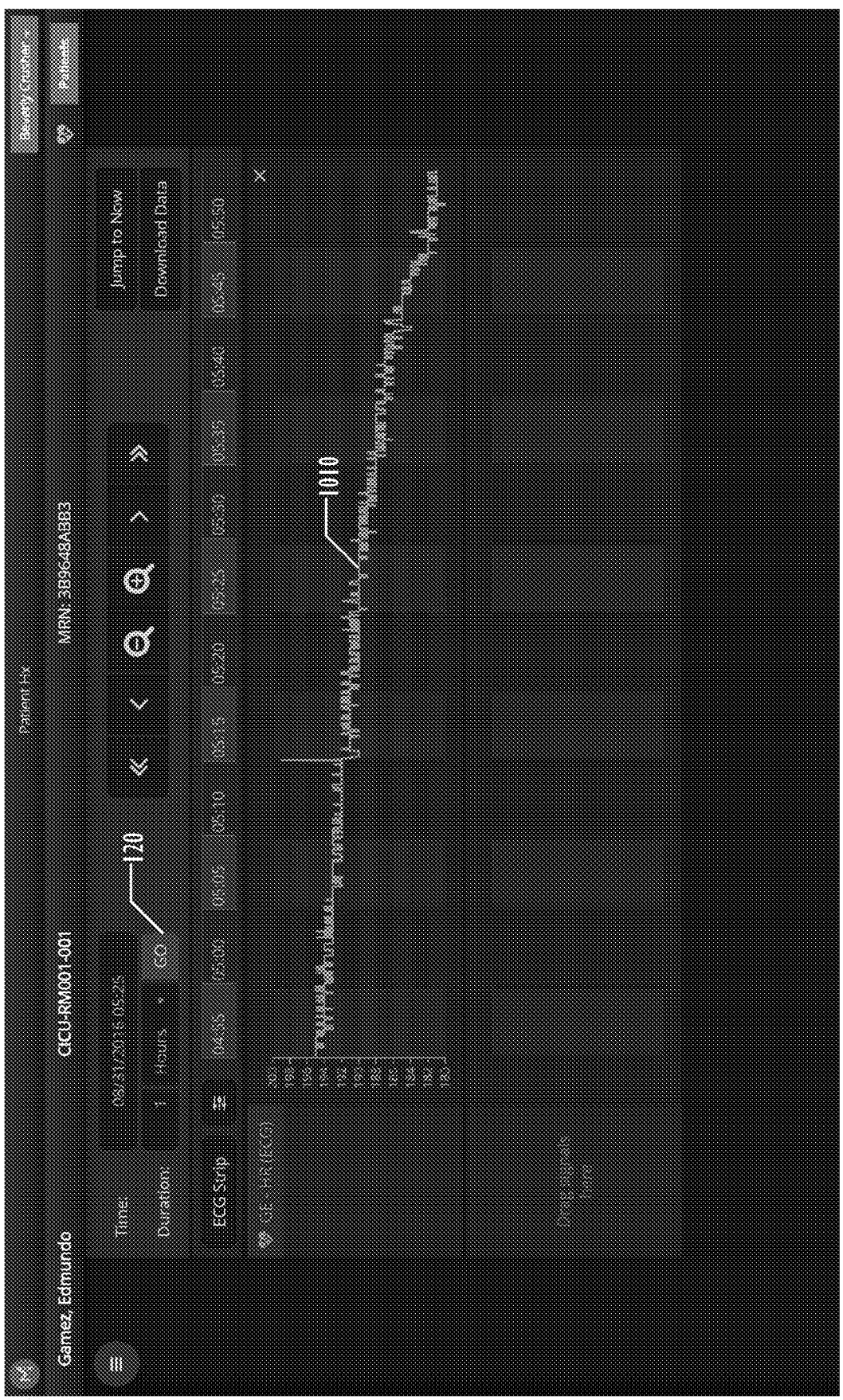
Figure 13:
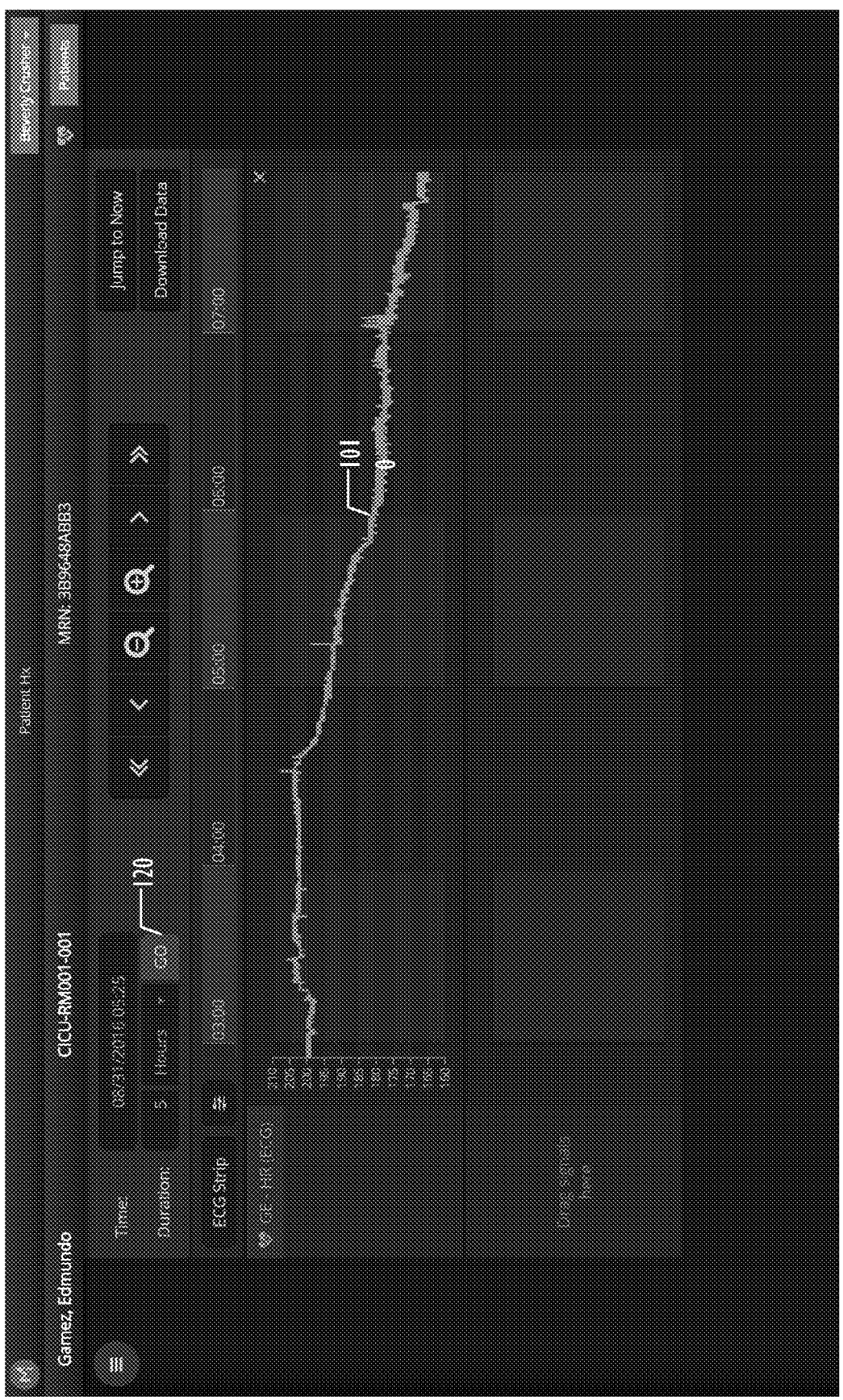
Figure 14:
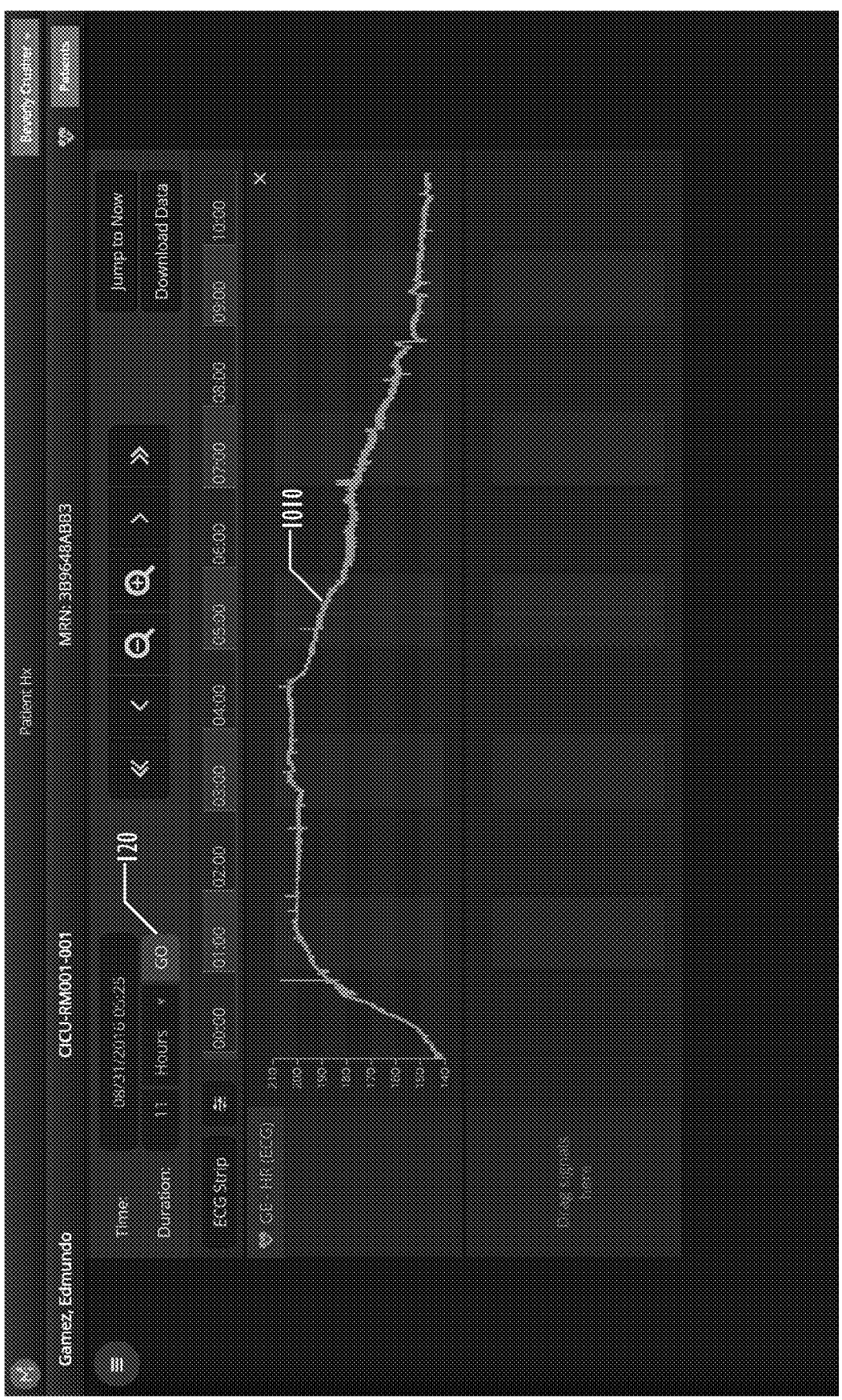

In addition to automatic amplitude scaling of the historical patient data, the GUI 100 in some embodiments may modify the display of the historical patient data based on the duration. FIGS. 10-15 illustrate this modification. In FIG. 10, an ECG lead waveform 1010 is displayed with a 10 minute duration, resulting in one minute time slots, with a high resolution providing a lot of detail. As the duration increases in FIGS. 11-14 (FIG. 11: 30 minutes, FIG. 12: 1 hour, FIG. 13: 5 hours, and FIG. 14: 11 hours, as illustrated in duration widget 120), more and more of the ECG waveform 1010 continues to be displayed, but with successively lower resolution, and thus less visible detail.

Figure 15:
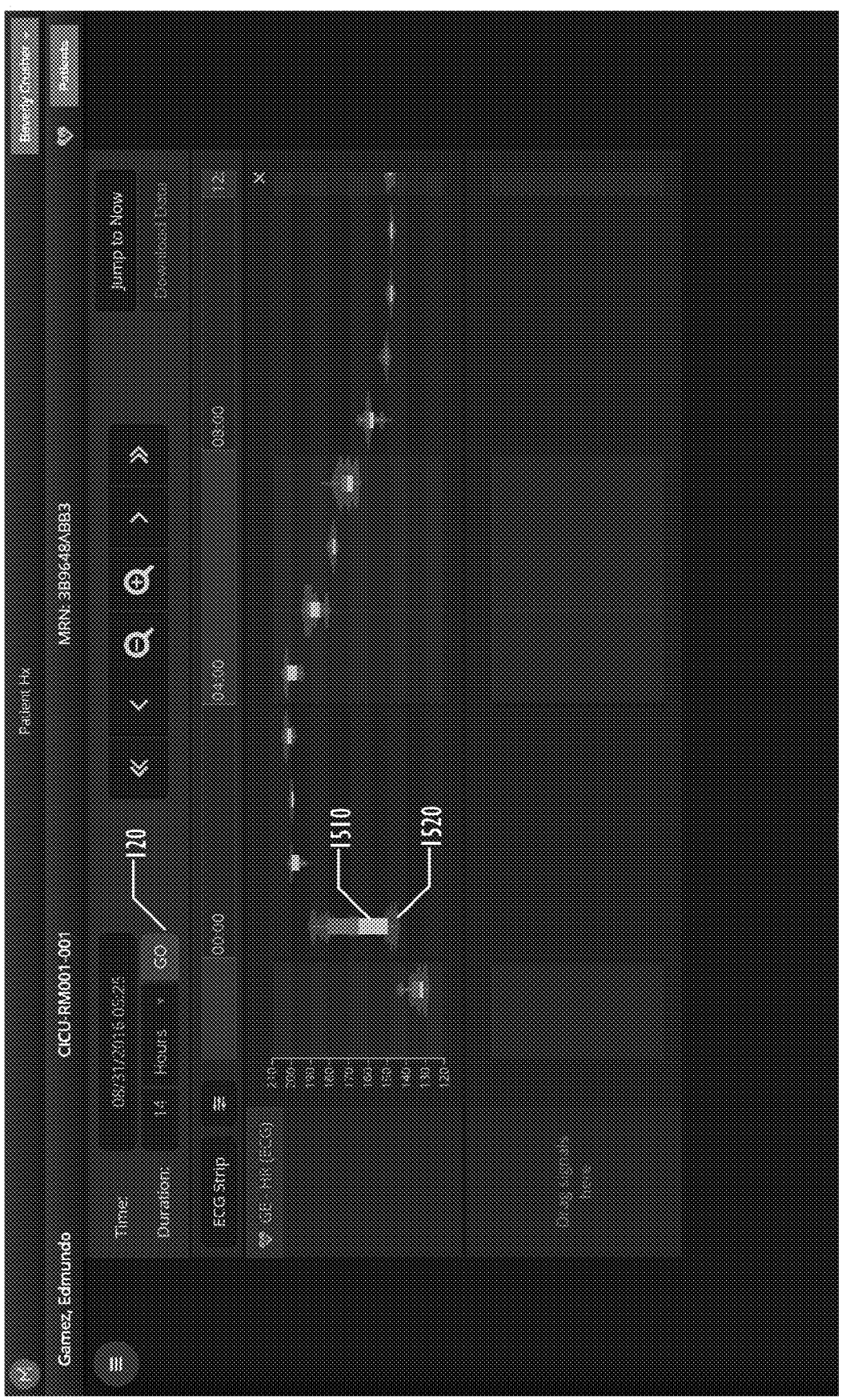

In FIG. 15, the duration has increased to 14 hours, which would result in a low resolution waveform largely looking like a smooth line, with very little detail. To provide some of the detail lost in the low resolution waveform, at a certain threshold duration, in one embodiment configurable by the actor, the waveform display is changed to a display of box plots and violin plots at sub-intervals along the timeline. In one embodiment, the switch to between displaying waveforms and box plots automatically occurs at any time over a 12 hour duration.

Box plots, sometimes known as Tukey box plots because they were introduced by John W. Tukey in 1969, are a technique for graphically depicting groups of numerical data through their quartiles. Box plots are non-parametric: they display variation in samples of a statistical population without making any assumptions of the underlying statistical distribution. The spacings between the different parts of the box indicate the degree of dispersion (spread) and skewness in the data, and show outliers. They allow the actor to visually estimate various L-estimators, notably the interquartile range, midhinge, range, mid-range, and trimean. The bottom of the box indicates the third quartile and the top of the box indicates the first quartile, while a band or change between the top and bottom indicates the second quartile or median.

In the example of FIG. 15, the portion of the box plot above the median is indicated in blue, while the portion below the median is shown in white for ease of distinguishing them. Those colors are illustrative and by way of example only, and other colors could be used, or the median position could be indicated by a line across the box. In some embodiments, whisker lines extend from the box 1510 to indicate additional information, such as the minimum and maximum values for the historical patient data at that position on the timeline or a 5% and 95% confidence level; other configurations of the whisker lines can be used. In some embodiments, a crosshatch may be placed on each whisker at the end of the whisker for each of seeing the extent of the whisker. Other types of box plots can be used as desired. For example, although the box plots of FIG. 15 are fixed width box plots, embodiments may include variable width box plots that can illustrate the size of the group whose data is plotted by the box, or notched box plots that have a notch or narrowing of the box around the median, providing a rough guide to the significance of differences of medians.

Figure 16:
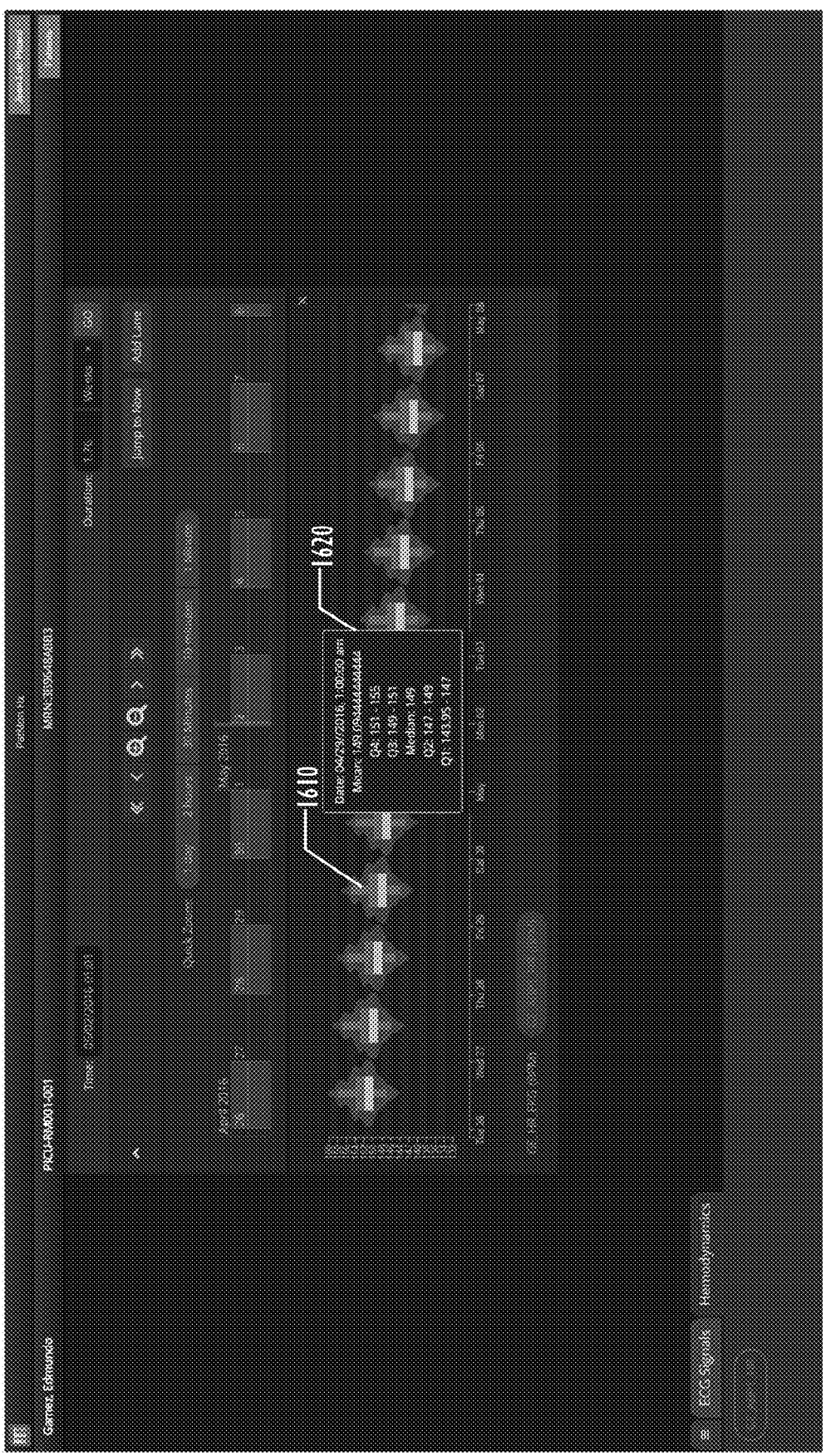
FIG. 16 is a screenshot illustrating a user interface according to another embodiment illustrating historical patient data in box plot form according to one embodiment.

In one embodiment, illustrated in FIGS. 15 and 16, violin plots 1520 are superimposed on the box plots 1510. A violin plot is a method of plotting numeric data that is similar to a box plot with a rotated kernel density plot on each side. The violin plot shows the probability density of the data at different values, thus helps the actor visualize the distribution of the data and its probability density. Other embodiments could omit the violin plots 1520 and just display the box plots 1510.

FIG. 16 is screenshot of an alternate embodiment showing box plots and violin plots. In this screenshot, an actor has selected one of the box plots 1610 causing a popup display 1620 of statistical information corresponding to that box plot, in this example providing a date and time, mean, median, and first, second, third, and fourth quartiles value ranges for the historical patient data.

In some embodiments, the GUI 100 may also provide access to help or tutorial information, either as part of the GUI system or in a third party provided knowledge base such as the FRESHDESK® knowledge base. (FRESHDESK is a registered trademark of FreshDesk Inc.

Figure 17:
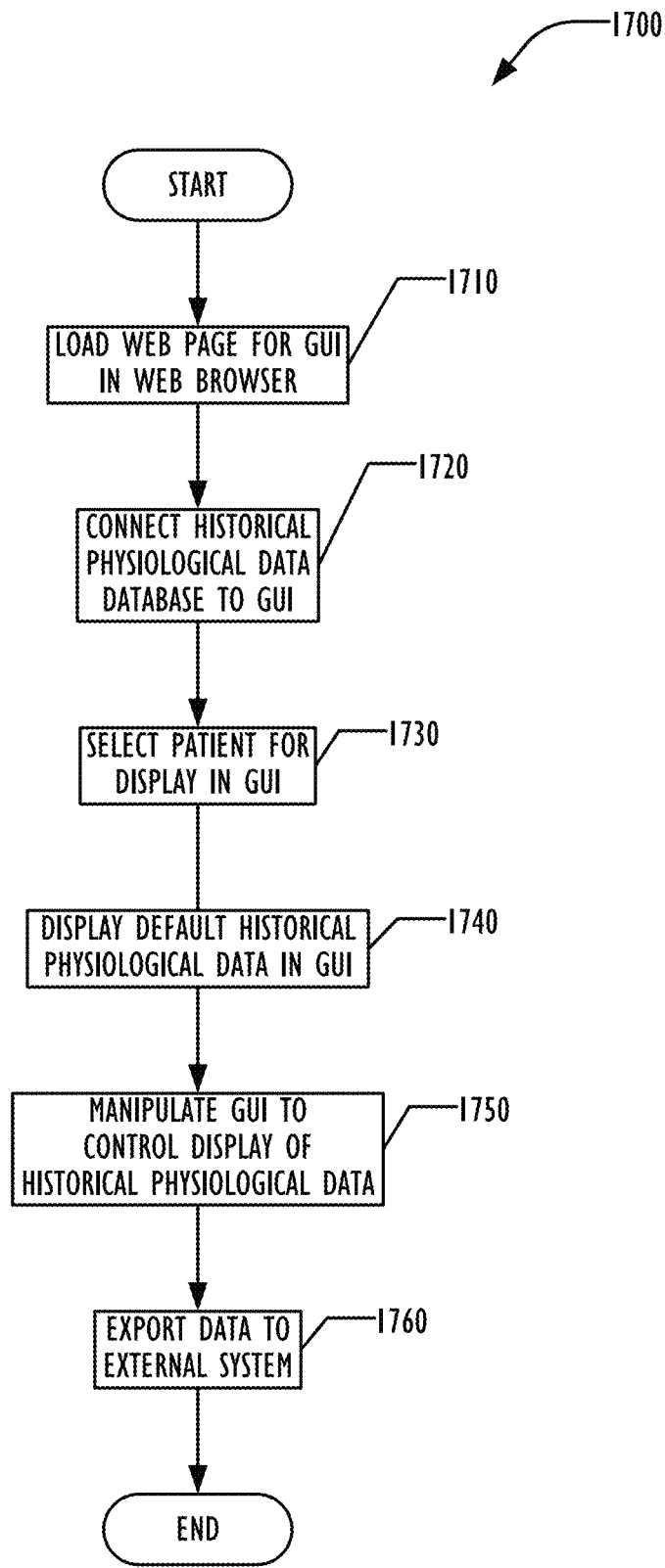
FIG. 17 is a flowchart illustrating a procedure for displaying and manipulating historical patient data in a graphical user interface according to one embodiment.

FIG. 17 is a flowchart 1700 illustrating a flow of events related to use of the GUI 100 described above. In block 1710, an actor loads the web page for the GUI 100 in a web browser. This may be done by clicking on a link in another application that takes the actor to the historical patient data web page. In block 1720, a database of historical patient data is connected to the GUI 100 to allow the actor in block 1730 to select a patient for viewing as described above. Upon opening the historical patient data for the selected patient in the GUI 100, a default view of the patient's data may be provided in the GUI 100 in block 1740, such as the last 12 hours of data for a default data signal. These defaults may be configured by the actor and in some embodiments, the clinical facility may provide facility-wide defaults for use unless the actor has established custom defaults.

In block 1750, the actor may manipulate the GUI 100 in any of the ways described above to select the historical patient data to be viewed, the duration of the time period to be viewed, zoom level, etc. In some embodiments, GUI 100 settings may be retained from session to session, so that the actor may set actor-specific or patient-specific default views of historical patient data.

In block 1760, the actor may choose to print or export some or all of the historical patient data to a system external to the GUI 100 for additional review or analysis. For example, in some embodiments the historical patient data can be exported to an electronic medical records (EMR) system.

Figure 18:
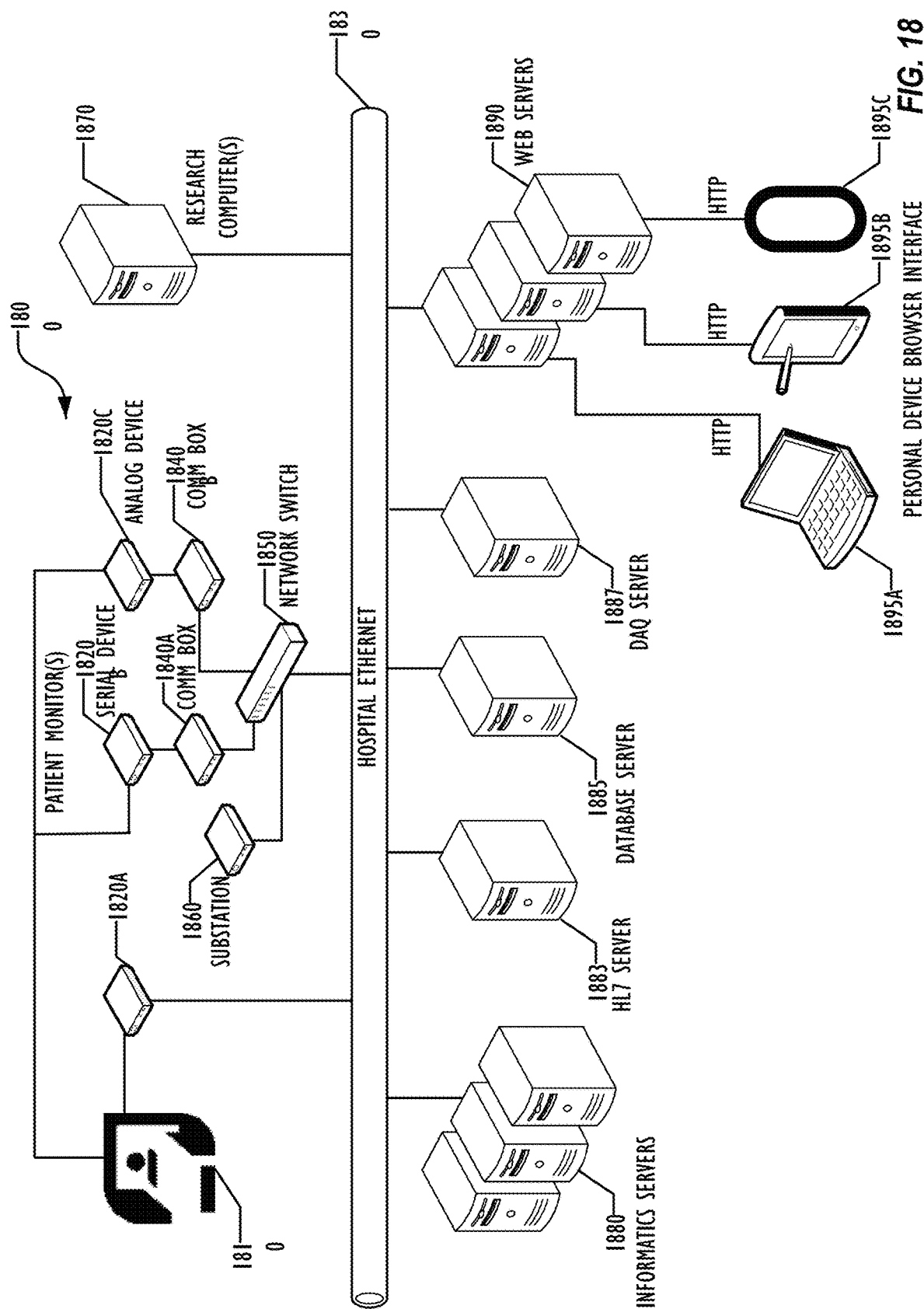
FIG. 18 is block diagram illustrating a network of devices employed by a hospital system according to one embodiment.

FIG. 18 is a block diagram illustrating a system 1800 for collecting, archiving, and processing arbitrary data in a healthcare environment that can deploy a user interface as described above, according to one embodiment.

As illustrated, there are five types of servers: the data acquisition (DAQ) server 1887, the informatics server(s) 1880, the database server 1885, the Health Level 7 (HL7) server 1883, and the web server(s) 1890. Any number of any of the types of servers may be deployed as desired. All of the servers 1880-1890 connect to each other and the bedside monitors via one or more hospital networks 1830. Although illustrated as a single hospital Ethernet network 1830, any number of interconnected networks may be used, using any desired networking protocols and techniques.

Also connected to the hospital network 1830 are a number of bedside monitors for monitoring physiological data for a patient in bed 1810. These bedside monitors may include network connected monitors 1820A, which can deliver digital physiological data to the hospital network 1830, serial devices 1820B, which produce digital data but are not directly connected to a network, and analog devices 1820C, which produce analog data and are not directly connected to a network. Communication boxes 1840A and 1840B allow connecting the serial devices 1820B and analog devices 1820C, respectively, to the hospital network 1830, typically through a network switch 1850. In addition, a substation 1860 may be also connected to the network 1830 via the network switch 1850 for performing data manipulation and time synchronization as described below. Any number of bedside monitors 1820 may be used as determined advisable by physicians and other clinical staff for the patient in bed 1810.

Although as illustrated in FIG. 18 the bedside monitors and associated communication devices are connected directly or indirectly to the hospital network 1830, remote bedside monitoring devices may be used as part of the system 1800, such as home monitoring devices, connected to the hospital network 1830 indirectly through the Internet or through other communication techniques.

Additionally, one or more research computers 1870 may be connected, directly or indirectly, to the hospital network 1830, allowing researchers to access aggregated data collected from bedside monitors 1820 for performing analytics and development.

The database server 1885 is configured for storage of historical patient data databases, which can be connected to the historical patient data graphical interface 100 for displaying historical patient data.

The web servers 1890 are configured for communicating with personal devices such as laptop 1895A, tablet 1895B, or smart phone 1895C via a web browser interface using HyperText Transport Protocol (HTTP).

Figure 19:
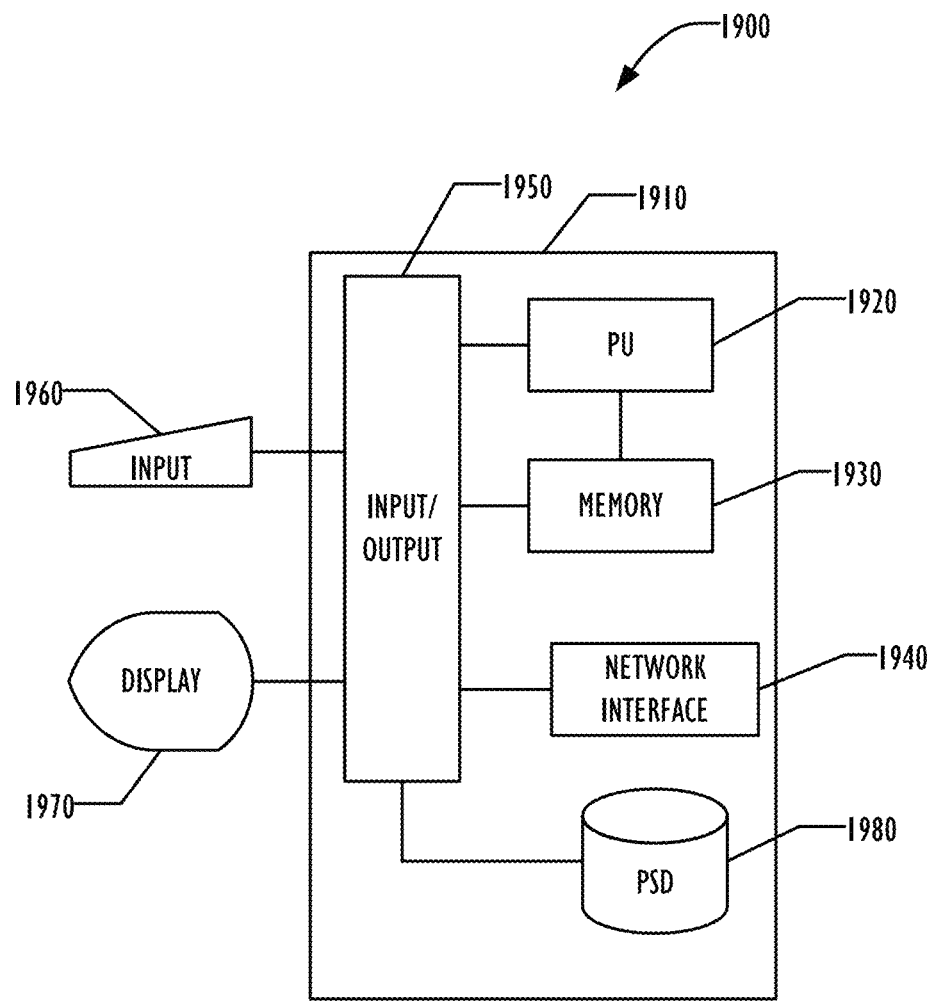
FIG. 19 is a block diagram illustrating a computer system for use in implementing one or more embodiments.

Referring now to FIG. 19, an example computer 1900 for use as one of the servers 480-490 is illustrated in block diagram form. Example computer 1900 comprises a system unit 1910 which may be optionally connected to an input device or system 1960 (e.g., keyboard, mouse, touch screen, etc.) and display 1970. A program storage device (PSD) 1980 (sometimes referred to as a hard disc) is included with the system unit 1910. Also included with system unit 1910 is a network interface 1940 for communication via a network with other computing and corporate infrastructure devices (not shown). Network interface 1940 may be included within system unit 1910 or be external to system unit 1910. In either case, system unit 1910 will be communicatively coupled to network interface 1940. Program storage device 1980 represents any form of non-volatile storage including, but not limited to, all forms of optical and magnetic, including solid-state, storage elements, including removable media, and may be included within system unit 1910 or be external to system unit 1910. Program storage device 1980 may be used for storage of software to control system unit 1910, data for use by the computer 1900, or both.

System unit 1910 may be programmed to perform methods in accordance with this disclosure. System unit 1910 comprises a processor unit (PU) 1920, input-output (I/O) interface 1950 and memory 1930. Processor unit 1920 may include any programmable controller device, such as microprocessors available from Intel Corp. and other manufacturers. Memory 1930 may include one or more memory modules and comprise random access memory (RAM), read only memory (ROM), programmable read only memory (PROM), programmable read-write memory, and solid-state memory. One of ordinary skill in the art will also recognize that PU 1920 may also include some internal memory including, for example, cache memory.

Embodiments may be implemented in one or a combination of hardware, firmware, and software. Embodiments may also be implemented as instructions stored on a computer-readable storage medium, which may be read and executed by at least one processing element to perform the operations described herein. A computer-readable storage medium may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

Embodiments, as described herein, may include, or may operate on, logic or a number of components, modules, or mechanisms. Modules may be hardware, software, or firmware communicatively coupled to one or more processing elements in order to carry out the operations described herein. Modules may be hardware modules, and as such, modules may be considered tangible entities capable of performing specified operations and may be configured or arranged in a certain manner. Circuits may be arranged (e.g., internally or with respect to external entities such as other circuits) in a specified manner as a module. The whole or part of one or more programmable devices (e.g., a standalone client or server computer system) or one or more hardware processing elements may be configured by firmware or software (e.g., instructions, an application portion, or an application) as a module that operates to perform specified operations. The software may reside on a computer readable medium. The software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Where modules are temporarily configured, each of the modules need not be instantiated at any one moment in time. For example, where the modules comprise a general-purpose hardware processing element configured using software; the general-purpose hardware processing element may be configured as respective different modules at different times. Software may accordingly program a hardware processor, for example, to constitute a particular module at one instance of time and to constitute a different module at a different instance of time. Modules may also be software or firmware modules, which operate to perform the methodologies described herein.

While certain exemplary embodiments have been described in details and shown in the accompanying drawings, it is to be understood that such embodiments are merely illustrative of and not devised without departing from the basic scope thereof, which is determined by the claims that follow.

We claim:

1. A medical patient monitoring system, comprising:
   one or more processors; and
   a memory, coupled to the one or more processors, on which are stored instructions for receiving and displaying patient historical data, comprising instructions that when executed cause the one or more processors to:
   receive historical patient data associated with a patient; and
   display a predetermined time interval of a selected historical patient data as a graph in a web-based graphical user interface;
   modify a zoom level responsive to a zoom widget;
   switch the graph displaying the selected historical patient data from a waveform to a sequence of box plots and violin plots that indicate distribution information corresponding to the box plots for time sub-intervals automatically, responsive to the modified zoom level exceeding a threshold zoom level;
   switch the graph displaying the selected historical patient data from the sequence of box plots and violin plots to a waveform automatically, responsive to the modified zoom level not exceeding the threshold zoom level; and
   responsive to a selection of one of the box plots, display statistical information that was used for generating the selected box plot.

2. The medical patient monitoring system of claim 1, wherein the instructions that when executed cause the one or more processors to display the selected historical patient data in the graphical user interface comprise instructions that when executed cause the one or more processors to pan or scroll the historical patient data responsive to a user input.

3. The medical patient monitoring system of claim 1, wherein the instructions that when executed cause the one or more processors to display the selected historical patient data in the graphical user interface comprise instructions that when executed cause the one or more processors to display alarm limits corresponding to the selected historical patient data.

4. The medical patient monitoring system of claim 1, wherein the instructions further comprise instructions that when executed cause the one or more processors to plot patient related events in the graphical user interface.

5. The medical patient monitoring system of claim 4, where the patient related events comprise lab results or provision of medication to the patient.

6. The medical patient monitoring system of claim 1, wherein the instructions that when executed cause the one or more processors to display the selected historical patient data in the graphical user interface comprise instructions that when executed cause the one or more processors to display patient electrocardiogram data as a strip view in the graphical user interface, the strip view configured to correspond to a strip print from an electrocardiogram device.

7. The medical patient monitoring system of claim 6, wherein the instructions that when executed cause the one or more processors to display the patient electrocardiogram data in a strip view comprise instructions that when executed cause the one or more processors to display a pair of caliper lines on the strip view, wherein the strip view is pannable or scrollable under the pair of caliper lines.

8. The medical patient monitoring system of claim 1, wherein the instructions that when executed cause the one or more processors to display the predetermined time interval of the selected historical patient data comprise instructions that when executed cause the one or more processors to scale the selected historical patient data automatically.

9. The medical patient monitoring system of claim 1, wherein the instructions that when executed cause the one or more processors to display the predetermined time interval of the selected historical patient data comprise instructions that when executed cause the one or more processors to display a plurality of types of historical patient data superimposed on each other, automatically scaled to display the plurality of historical patient data.

10. The medical patient monitoring system of claim 1, wherein the instructions that when executed cause the one or more processors to display the selected historical patient data in the graphical user interface comprise instructions that when executed cause the one or more processors to display alarm data as histograms of alarm levels.

11. The medical patient monitoring system of claim 1, wherein the instructions that when executed cause the one or more processors to display the selected historical patient data in the graphical user interface comprise instructions that when executed cause the one or more processors to display a pair of calipers at a caliper width and a sequence of shadow calipers spaced apart at the caliper width along the displayed selected historical patient data.

12. The web-based medical patient monitoring system of claim 1, wherein the statistical information comprises one or more of date and time, mean, median, and first, second, third, and fourth quartiles value ranges for the historical patient data used for generating the selected box plot.

13. A method of monitoring a medical patient, comprising:
selecting an historical patient data type from a plurality of available historical patient data types;
displaying historical patient data of the selected historical patient data type as a graph in a web-based graphical user interface;
modifying a zoom level responsive to a zoom widget;
switching the graph displaying the historical patient data from a waveform to a sequence of box plots and violin plots that indicate distribution information corresponding to the box plots for time sub-intervals automatically, responsive to the modified zoom level exceeding a threshold zoom level;
switching the graph displaying the historical patient data from the sequence of box plots and violin plots to a waveform automatically, responsive to the modified zoom level not exceeding the threshold zoom level; and
displaying, responsive to a selection of one of the box plots, statistical information that was used for generating the selected box plot.

14. The method of claim 13, further comprising displaying alarm limits corresponding to the historical patient data.

15. The method of claim 13, further comprising:
displaying non-waveform patient related events in the graphical user interface.

16. The method of claim 13, wherein selecting the historical patient data type from the plurality of available historical patient data types comprises:
displaying available types of historical patient data in the graphical user interface; and
selecting a type of historical patient data from the available types of historical patient data for display in the graphical user interface, responsive to a user input.

17. The method of claim 13, wherein the historical patient data comprises electrocardiogram data, further comprising:
displaying the electrocardiogram data as an electrocardiogram strip view.

18. The method of claim 17, further comprising: autoscaling the electrocardiogram data.

19. The method of claim 17, further comprising: displaying a pair of caliper lines in the electrocardiogram strip view.

20. The method of claim 19, further comprising: panning or scrolling the electrocardiogram strip view under the pair of caliper lines.

21. The method of claim 13, further comprising displaying a plurality of types of historical patient data superimposed on each other and automatically scaled.

22. The method of claim 13, wherein the historical patient data comprises historical patient alarm data.

23. The method of claim 22, wherein displaying the historical patient data comprises displaying histograms of the historical patient alarm data.

24. The method of claim 15, wherein the non-waveform patient related events comprise lab results or provisioning of medication.

25. The method of claim 13, further comprising:
displaying a pair of caliper lines at a caliper width on the historical patient data;
displaying a sequence of shadow calipers spaced apart the caliper width on the historical patient data; and
removing the pair of caliper lines and the sequence of shadow calipers.

26. The method of claim 13, further comprising selecting a patient in the graphical user interface, where the historical patient data corresponds to the selected patient.

27. The method of claim 13, wherein the statistical information comprises one or more of date and time, mean, median, and first, second, third, and fourth quartiles value ranges for the historical patient data used for generating the selected box plot.

28. A non-transitory computer readable medium, on which are stored instructions for monitoring medical patient historical information, comprising instructions that when executed cause a medical patient monitoring system to:
receive historical patient data associated with a patient;
display a predetermined time interval of a selected historical patient data as a graph in a web-based graphical user interface,
modify a zoom level of the historical patient data responsive to a zoom widget,
switch the graph displaying the selected historical patient data to a sequence of box plots and violin plots that indicate distribution information corresponding to the box plots for time sub-intervals automatically, responsive to the modified zoom level exceeding a threshold zoom level,
switch the graph displaying the selected historical patient data from the sequence of box plots and violin plots to a waveform automatically, responsive to the modified zoom level not exceeding the threshold zoom level, and
responsive to a selection of one of the box plots, display statistical information that was used for generating the selected box plot.

29. The non-transitory computer readable medium of claim 28, wherein the instructions further comprise instructions that when executed cause the medical patient monitoring system to pan or scroll historical patient data responsive to user input.

30. The non-transitory computer readable medium of claim 28, wherein the instructions further comprise instructions that when executed cause the medical patient monitoring system to:
display alarm limits corresponding to the selected historical patient data.

31. The non-transitory computer readable medium of claim 28, wherein the instructions further comprise instructions that when executed cause the medical patient monitoring system to:
plot patient related events in the graphical user interface.

32. The non-transitory computer readable medium of claim 31, wherein the patient related events comprise lab results or provision of medication.

33. The non-transitory computer readable medium of claim 28, wherein the historical patient data comprises electrocardiogram data, and wherein the instructions that when executed cause the medical patient monitoring system to display the historical patient data in an electrocardiogram strip view.

34. The non-transitory computer readable medium of claim 33, wherein the graphical user interface further comprises a pair of calipers placed responsive to user input.

35. The non-transitory computer readable medium of claim 28, wherein the statistical information comprises one or more of date and time, mean, median, and first, second, third, and fourth quartiles value ranges for the historical patient data used for generating the selected box plot.

* * * * *